(12) United States Patent
West et al.

(10) Patent No.: US 11,596,478 B2
(45) Date of Patent: Mar. 7, 2023

(54) CHARACTERIZING BEHAVIOR OF ANATOMICAL STRUCTURES

(71) Applicant: THE CLEVELAND CLINIC FOUNDATION, Cleveland, OH (US)

(72) Inventors: Karl West, Cleveland, OH (US); Vikash Goel, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 754 days.

(21) Appl. No.: 16/483,855

(22) PCT Filed: Feb. 5, 2018

(86) PCT No.: PCT/US2018/016796
§ 371 (c)(1),
(2) Date: Aug. 6, 2019

(87) PCT Pub. No.: WO2018/144969
PCT Pub. Date: Aug. 9, 2018

(65) Prior Publication Data
US 2020/0022757 A1    Jan. 23, 2020

Related U.S. Application Data

(60) Provisional application No. 62/455,140, filed on Feb. 6, 2017.

(51) Int. Cl.
*A61B 34/10* (2016.01)
*A61B 5/00* (2006.01)
(Continued)

(52) U.S. Cl.
CPC ............ *A61B 34/10* (2016.02); *A61B 5/0205* (2013.01); *A61B 5/062* (2013.01); *A61B 5/6851* (2013.01);
(Continued)

(58) Field of Classification Search
CPC ....... A61B 34/10; A61B 5/0205; A61B 5/062; A61B 5/6851; A61B 5/6859;
(Continued)

(56) References Cited

U.S. PATENT DOCUMENTS

| 2008/0139915 A1* | 6/2008 | Dolan | A61B 34/20 600/407 |
|---|---|---|---|
| 2011/0026793 A1* | 2/2011 | Goel | G06T 7/60 382/131 |

(Continued)

FOREIGN PATENT DOCUMENTS

EP    1504713 A1    2/2005

OTHER PUBLICATIONS

Choi, Gilwoo, et al. "Methods for quantifying three-dimensional deformation of arteries due to pulsatile and nonpulsatile forces: implications for the design of stents and stent grafts." Annals of biomedical engineering 37.1 (2009): 14-33.

(Continued)

*Primary Examiner* — Erin M Piateski
(74) *Attorney, Agent, or Firm* — Tarolli, Sundheim, Covell & Tummino LLP

(57) ABSTRACT

This disclosure relates generally to systems and methods for characterizing a behavior of an anatomical structure. Tracking data can be generated by a tracking system to represent at least a location of at least one sensor in a three-dimensional tracking coordinate system over time. A motion model is generated to characterize the behavior of the anatomical structure over a plurality of time instances. For instance, the motion model includes at least one free parameter and a temporal parameter. Each free parameter estimating geometry of the anatomical structure derived from the tracking data, and the temporal parameter indexes the free parameter over the plurality of time instances. A visualiza- (Continued)

tion is generated to provide a sequence of graphical images based on the motion model to characterize behavior of the anatomical structure over time.

29 Claims, 12 Drawing Sheets

(51) Int. Cl.
| | |
|---|---|
| *A61B 5/0205* | (2006.01) |
| *A61B 5/06* | (2006.01) |
| *G16H 15/00* | (2018.01) |
| *G16H 30/20* | (2018.01) |
| *A61B 90/00* | (2016.01) |
| *A61B 5/11* | (2006.01) |
| *A61B 5/113* | (2006.01) |
| *A61B 17/00* | (2006.01) |

(52) U.S. Cl.
CPC .......... *A61B 5/6859* (2013.01); *G16H 15/00* (2018.01); *G16H 30/20* (2018.01); *A61B 5/1102* (2013.01); *A61B 5/113* (2013.01); *A61B 2017/00699* (2013.01); *A61B 2017/00703* (2013.01); *A61B 2017/00778* (2013.01); *A61B 2034/105* (2016.02); *A61B 2090/364* (2016.02); *A61B 2505/05* (2013.01)

(58) Field of Classification Search
CPC ........ A61B 2034/105; A61B 2090/364; A61B 5/1102; A61B 5/113; A61B 2017/00699; A61B 2017/00703; A61B 2017/00778; A61B 2505/05; G16H 15/00; G16H 30/20
USPC ........................................................ 600/301
See application file for complete search history.

(56) References Cited

U.S. PATENT DOCUMENTS

| | | | |
|---|---|---|---|
| 2014/0276002 A1 | 9/2014 | West et al. | |
| 2015/0289929 A1* | 10/2015 | Toth | A61B 5/6852 606/41 |
| 2016/0066794 A1* | 3/2016 | Klinder | A61B 5/02028 600/424 |
| 2016/0239963 A1* | 8/2016 | Kariv | A61B 5/283 |

OTHER PUBLICATIONS

PCT International Search Report and Written Opinion for corresponding International Application Serial No. PCT/US2018/016796, dated Apr. 19, 2018, pp. 1-14.

Suh, Ga-Young, et al. "Aortic arch vessel geometries and deformations in patients with thoracic aortic aneurysms and dissections." Journal of Vascular and Interventional Radiology 25.12 (2014): 1903-1911.

Suh, Ga-Young, et al. "Respiration-induced deformations of the superior mesenteric and renal arteries in patients with abdominal aortic aneurysms." Journal of Vascular and Interventional Radiology 24.7 (2013): 1035-1042.

* cited by examiner

CHARACTERIZING BEHAVIOR OF ANATOMICAL STRUCTURES

RELATED APPLICATIONS

This application is a national phase application of and claims priority from PCT International Patent Application PCT/US2018/016796, filed Feb. 5, 2018, which claims the benefit of priority from U.S. Provisional Application No. 62/455,140, filed Feb. 6, 2017 and entitled CHARACTERIZING A BEHAVIOR OF AN ANATOMICAL STRUCTURE. Each of the above-identified applications is incorporated herein by reference in its entirety.

TECHNICAL FIELD

This disclosure relates generally to systems, methods and devices for characterizing a behavior of an anatomical structure, such an endovascular structure.

BACKGROUND

Understanding how a vascular structure, such as a blood vessel (e.g., artery and vein), behaves is of interest to medical staff (e.g., a surgeon). Various imaging methodologies can assess the behavior of the vascular structures. However, many existing imaging methodologies, such as X-Ray fluoroscopy, expose both patients and caregivers to ionizing radiation. Additionally, many existing imaging modalities are unable to adequately visualize, in real-time, behaviors exhibited by vascular and other structures, for example, intraprocedurally, without the use of contrast dyes. In many cases, the resulting images may provide poor visualizations and, therefore, be insufficient to provide actionable guidance, especially in the case of complex anatomy or advanced procedures.

SUMMARY

As one example, a system is disclosed to characterize motion of an anatomical structure. The system includes a sensor attached to an apparatus, which is configured for insertion within the anatomical structure. A tracking system generates tracking data representing at least a position of the sensor in a three-dimensional tracking coordinate system over time. A computing device includes a processor to execute machine-readable instructions to compute a motion model characterizing a behavior of the anatomical structure over a time interval based on at least one free parameter and a temporal parameter. The free parameter estimates geometry of the anatomical structure derived from the tracking data. The temporal parameter indexes the free parameter over the time interval. The instructions are also programmed to generate a graphical representation of the motion model to visualize the behavior of the anatomical structure over the time interval.

As another example, a method includes storing tracking data generated by a tracking system to represent at least a location of at least one sensor in a three-dimensional tracking coordinate system over time. A motion model is generated to characterize the behavior of the anatomical structure over a plurality of time instances. For instance, the motion model includes at least one free parameter and a temporal parameter. Each free parameter estimating geometry of the anatomical structure derived from the tracking data, and the temporal parameter indexes the free parameter over the plurality of time instances. A visualization is generated to provide a sequence of graphical images based on the motion model to characterize behavior of the anatomical structure over time.

DETAILED DESCRIPTION

Figure 1:
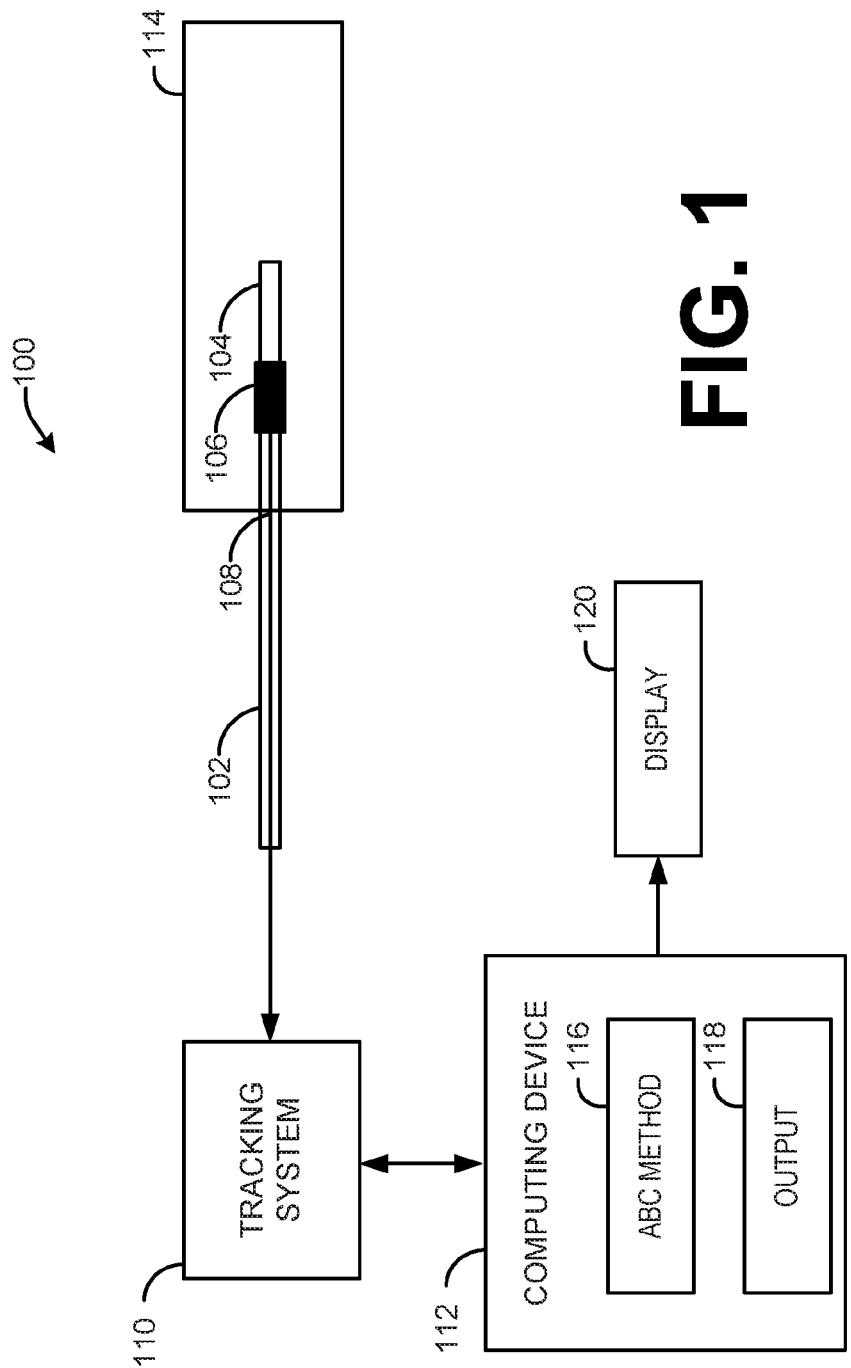
FIG. 1 depicts an example of a system to characterize anatomical behavior of an anatomical structure.

This disclosure relates generally to systems, methods and devices for characterizing a behavior of an anatomical structure, such an endovascular structure (e.g., a vessel, such as the aorta) or tubular structure (e.g., the esophagus, intestines or the like). In some examples, the behavior of the anatomical structure may exhibit a cyclic or periodic motion relative to one or more other anatomic functions. For example, the cyclic anatomical function of breathing (e.g., the respiratory cycle) may result in motion of the aorta, renal arteries or other anatomical structure that varies as a function of the respiratory cycle. Additionally or alternatively, the cardiac cycle may cause the aorta or other anatomical structures to move commensurate with each heart beat. The motion of these and other anatomical structures thus may be captured by a tracking system in the absence of ionizing radiation and gated to sensor signals for an anatomical function.

As an example, the systems and methods described herein can be employed during a medical procedure, such as an endovascular procedure. An object (e.g., an apparatus, such as a guidewire within a catheter) including one or more sensors can be deployed within the anatomical structure and thereby be affixed and configured to move commensurate with motion of the anatomical structure over time. As an example, the sensors may be electromagnetic (EM) sensors, such as electrically conductive sensor coils distributed along a length of the guidewire.

A tracking system generates tracking data representing a position and/or orientation of each sensor in a three-dimensional tracking coordinate system over time. As mentioned, the sensors fixed relative to such structure may move within the patient's body commensurate with one or more cyclical anatomical functions (e.g., respiratory or cardiac cycles). The tracking data may be evaluated to generate vessel characterization data associated with the position of the anatomical structure over time. For example, the locations and/or orientations of the sensors can be computed for each time sample, which can be used to compute a geometry of the guidewire or other apparatus to which the sensors are fixed. For example, one or more parametric models are generated to describe the geometry of the anatomical structure at each respective time sample. The computed geometry information over a series of time instances may be aggregated to generate anatomical characterization data, which can be rendered to provide a four-dimensional (4D) graphical representation visualizing changes in the spatial behavior of the anatomical structure over time.

As a further example, a 4D parametric motion model, corresponding to the vessel characterization data, may be computed to characterize the behavior of the anatomical structure over a time interval based on one or more free parameters and a temporal parameter. For example, each free parameter estimates the geometry of the anatomical structure derived from the tracking data, such as one or more spline functions describing the geometry of a centerline and/or geometry of a surface wall. The temporal parameter may represent a time interval of interest and/or a cyclical anatomical function that indexes the free parameter(s) over the time interval.

The 4D parametric model may be utilized to generate a graphical representation that visualizes changes in the behavior (e.g., spatial geometry) of the anatomical structure over time. For example, the 4D parametric model may be used as primitives to drive a graphics pipeline for rendering a corresponding visualization of anatomy that changes over time. The temporal parameter that indexes the parametric model may be correlated with phase of a temporal anatomical function, such as a cardiac cycle or a respiratory cycle, according to an input signal representing the anatomical function. For example, the cardiac cycle may be gated to an electrocardiogram (EKG) and the respiratory cycle may be gated to a respiratory input signal provided by a respiration monitor (e.g., a belt or other type of monitor). Thus, the anatomical behavior data characterizing the motion of the anatomical structure can be time-correlated with one or more anatomical functions and be stored in memory, such as for visualizing how the anatomy changes in response to such anatomical function. Such a correlation can provide a greater in depth understanding of how the cardiac and respiratory cycles or other anatomical functions of the patient impact motion of the anatomical structure.

As yet another example, the anatomical behavior of the structure (e.g., vessel) derived from the characterization data can be evaluated with respect to time to identify an impact that another implantable device has on the motion of the anatomical structure over time, including as such implantable device is positioned and moved within the anatomical structure. For example, a second set of characterization data may be generated from sensors on the implantable device (or on a guidewire that is within the implantable device) to record position and/or orientation information as it is advanced within the anatomical structure. A difference between the pre-placement characterization data (e.g., the 4D parametric mode) for the structure without the implantable device implanted in the structure and the second set of characterization data with the implantable device in the same structure may be determined and visualized to represent the difference over time. Motion data (e.g., three-dimensional image data) captured prior to placement of the implantable device relative to the anatomical structure can be used to derive one or more pre-placement parametric models of the anatomical structure. The pre-placement model may be evaluated relative to motion data captured after placement of the implantable device relative to the anatomical structure. In this way, changes in motion of the anatomical structure can be determined based on the evaluation and stored as deformation data in the memory over time and as a function of the relative position of the implantable device with respect to the anatomical structure as the device is advanced and/or withdrawn axially along the length of anatomical structure. The deformation data can be used to supplement and derive another parametric model for the anatomical structure that is used to characterize the anatomical model over time as the implantable device is moved with respect to the anatomical structure.

Additionally or alternatively, the systems and methods described herein can further be used to determine if the anatomical structure is exhibiting symptoms of dolichoectasia or another condition. Such systems and methods further may be used to identify areas of the anatomical structure exhibit torsion and/or translation in response to identified anatomical functions and/or the impact that an implantable device that traverses the structure. For example, the impact may be determined from a difference between the 4D model with and without the implantable device, which impact may be graphically rendered in the visualization. The visualization may be rendered according to color scale having values to represent the amount of torsion and/or translation that is being experienced in the anatomical structure.

FIG. 1 illustrates an example of an anatomical behavior characterization (ABC) system 100. The ABC system 100 can include an object 102 (e.g., a guidewire or a similar instrument). The object 102 can be used with an existing anatomical apparatus, such as a sheath and/or catheter (neither of which is shown in FIG. 1), for example, during a medical procedure. In one example, the medical procedure can be an endovascular procedure where the object 102 is navigated through a vascular anatomical structure 114. The endovascular procedure can include an abdominal aortic aneurysm (AAA) repair procedure, a renal artery stenting procedure or an aortic dissection repair procedure, among other procedures. In other examples, the procedure may involve temporary insertion of the objection into to any other tubular anatomical structure (e.g., bronchial tubes, esophagus, intestines or the like) 114.

By way of example, the object 102 can be inserted into a patient (e.g., human or animal) and navigated through one or more anatomical structures 114 of the patient. The one or more anatomical structures can comprise an elongated tubular vessel structure that includes a lumen, such as one or more endovascular structures (e.g., arteries or veins). Alternatively, the one or more anatomical structures can include at least one blood vessel, artery, part of a gastrointestinal tract, part of a respiratory tract or part of a reproductive tract. For example, the object 102 may be a guidewire having a distal end segment 104 that has a tapered inner core to enable torquability, trackability, pushability and crossability of the object 102 through the one or more anatomical structures. The guidewire 102 can be biocompatible and have a relative stiffness and compliance that is commensurate with an existing guidewire, such as a Glidewire® wire available from Terumo Corporation® or a Lunderquist® wire available from Cook Group, Inc.

The object 102 can include one or more sensors 106 detectable by an associated tracking system 110, which is configured to determine a position and/or orientation of each sensor in three-dimensional space (e.g., a coordinate system of the tracking system) in the absence of ionizing radiation. By way of example, the tracking system 110 can be an Aurora® EM tracking system from Northern Digital, Inc., a StealthStation® surgical navigation system from Medtronic, Inc.® or CARTO 3® electrode mapping system from Biosense Webster, Inc.®.

For example, the one or more sensors 106 can reside at select locations along a longitudinal portion of the object 102. For instance, the one or more sensors 106 can include a plurality of evenly spaced apart sensors distributed along an axis (e.g., a centerline) of the longitudinal portion of the distal end segment 104 of the object (e.g., guidewire) 102. Additionally or alternatively, a number of EM sensors fixed along the axis of the longitudinal portion of the object 102 can be a function of a length of the longitudinal portion. In some examples, each sensor can be detectable by the tracking system 110 to enable tracking in multiple (e.g, five or six) degrees of freedom. Examples of sensors that can be detected by an electromagnetic type of the tracking system 110 are sensor coils commercially available from Northern Digital, Inc., of Ontario, Canada. Other types of sensors 106 can be used depending on the type of tracking system.

In some examples, the object 102 can further include a set of two or more of legs (not shown in FIG. 1—but see, e.g., FIGS. 4-7) mechanically biased to extend radially outwardly from a first end at the guidewire and terminate in distal ends that engage contact locations along an interior wall of the anatomical structure 114. Each pair of diametrically opposed legs thus operate to retain the guidewire body at an intermediate location (e.g., centered) between the distal ends thereof. In this way, the legs operate to hold each sensor at a fixed position relative to the interior sidewall such that the sensors move commensurate with motion of the adjacent sidewall within the patient's body. For example, the legs may be formed of nitinol or another self-expanding (e.g., shape-memory alloy) material.

As an example, each of the legs (e.g., prongs or tines) can be configured to self-expand during a retraction of the existing anatomical device (e.g., catheter body or sheath) relative to the object 102 and collapse during an advancement of the catheter into engagement with and over the legs along the object 102. The legs can be configured to help prevent axial movement of the object 102 (e.g., by temporarily anchoring the legs to the vessel wall) while positioned at a given location of the anatomical structure.

In some examples, sensors may be located at sensor stations along the guidewire and held at or near the center of the lumen by the legs. Additionally or alternatively, the legs may include sensors at their distal ends that engage the contact locations along the interior wall of the anatomical structure. For example, a distance between each pair of the diametrically opposed sensors can be determined from the tracking data. This distance defines a diameter of the anatomical structure for the respective station, and the centerline of the lumen between sensors resides between the locations of the sensors. For example, the centerline location is calculated as a geometric mean of the position two or more sensors of an associated sensor station positioned along the lumen wall.

In some examples, the instrument 102 can further include one or more electrical leads 108. The one or more electrical leads 108 can couple each of the one or more sensors 106 to the tracking system 110. For example, the tracking system 110 can generate electrical magnetic (EM) fields within a spatial volume 3-D space (e.g., a 3-D tracking coordinate system) in which the object that is inserted into a patient's body resides. The EM fields generated by the tracking system can induce currents in the one or more EM sensors 106. These induced signals can be supplied via the one or more electrical leads 108 to the tracking system 110. A given amount of current induced at a respective EM sensor 106 at a given point in the patient space can be representative of a three-dimensional (3-D) position of the respective EM sensor 106 in the coordinate system of the tracking system space.

The tracking system 110 can determine in real-time (e.g., intraprocedurally) for the respective EM sensor 106 a 3-D position and orientation over time as the respective EM sensor 106 changes its position and/or orientation within the 3-D space based on the induced signals provided the respective EM sensor 106. The tracking system 110 can allow for dynamic real-time computations of each of sensors 106 position and/or orientation in the tracking system's coordinate system, while the one or more EM sensors 106 undergo movement over time, for example, in response to a change in spatial behavior of the anatomical structure. For example, the spatial behavior may be influenced by one or more voluntary or involuntary anatomical functions, such as respiration, beating of the heart, swallowing or the like. The tracking system 110 can supply to a computing device 112 tracking data derived in response to the sensor signals. The computing device position and/or orientation data characterizing the 3-D position and orientation for each of the plurality of EM sensors 106 over time. The computing device 112 can store in memory the position and/orientation data as tracking data.

The computing device 112 is programmed to include machine readable instructions executable by one or more processors (e.g., processor cores) that includes an ABC method 116. The ABC method 116 is programmed to generate a 4D characterization of the anatomical structure 114 based on the tracking data generated by the tracking system over time for each of the sensors 106. For example, the geometry of the anatomical structure 114 may include a centerline geometry and/or geometry of a lumen wall at each respective time instance in a time interval. As disclosed herein the time interval may be cyclical, such as corresponding to an anatomical function, such as respiration of cardiac cycles, and the ABC method 116 thus may characterize the geometry of the anatomical structure based on a temporal parameter representing one or more such cycles. The computing device 112 thus can store 4D ABC data in memory by aggregating ABC data generated (e.g., by ABC method 116) over a plurality of consecutive time instances in a given time interval. The ABC data can be supplied to a graphics pipeline to render a corresponding 4D graphical representation that visualizes behavior of the anatomical structure over time. As mentioned, the temporal parameter may correspond to a cyclical anatomical function, and the time instances of ABC data thus may be gated to an input signal representing such anatomical function and concatenated to visualize changes in the anatomical structure over time due to such anatomical function over a number of cycles.

In some examples, the ABC method generates the ABC data as a 4D parametric model characterizing the spatial behavior of the anatomical structure over one or more time intervals. The parametric model may employ one or more free parameters and a temporal parameter. The free parameter may estimate geometry of the anatomical structure in each of a plurality of time slices indexed according to the temporal parameter. For example, the free parameter may correspond to a linear free parameter that defines a shape of the centerline of the elongated, tubular anatomical structure that changes over the time interval according to the temporal parameter. Alternatively or additionally, the free parameter may correspond to a tangential free parameter that defines a cross-sectional shape of the anatomical structure that changes over the time interval according to the temporal parameter.

As disclosed herein, an output control 118 may process the parametric model (e.g., as primitives) via a graphics pipeline and generate a graphical representation to visualize on a display (e.g., a screen, heads-up display or the like) 120 the spatial behavior of the anatomical structure over time. The output control 118 may be implemented as hardware, firmware and/or software in the computing device 112. In some examples, the output control 118 may gate (e.g., synchronize) the 4D parametric model with a selected (e.g., user-selected) anatomical function, such as in response to an input signal representing the gating anatomical function, to visualize how the anatomical structure changes spatially in response to the anatomical function. To provide additional context for the visualization, the model may be registered into a common coordinate system with image data for the anatomical structure (e.g., based on anatomic landmarks) and the visualization of the motion model can be rendered as an overlay on the graphical representation on the image.

In some examples, the 4D parametric model may be combined with another parametric model that statically describes the anatomical structure such as has been derived from 3D image data (e.g., computed tomography (CT) scans, magnetic resonance imaging (MRI) scans or another imaging modality). For instance, the 4D parametric model may be registered into a common spatial coordinate system with the other parametric model (e.g., being previously derived in an offline process). The 4D parametric model thus can provide deformation parameters for at least a portion of the anatomical structure defined by the other parametric model and thereby enable a graphics pipeline to generate a 4D visualization showing behavior (e.g., cyclical behavior) of at least a portion of the anatomical structure over time based on the acquired tracking data.

Figure 2:
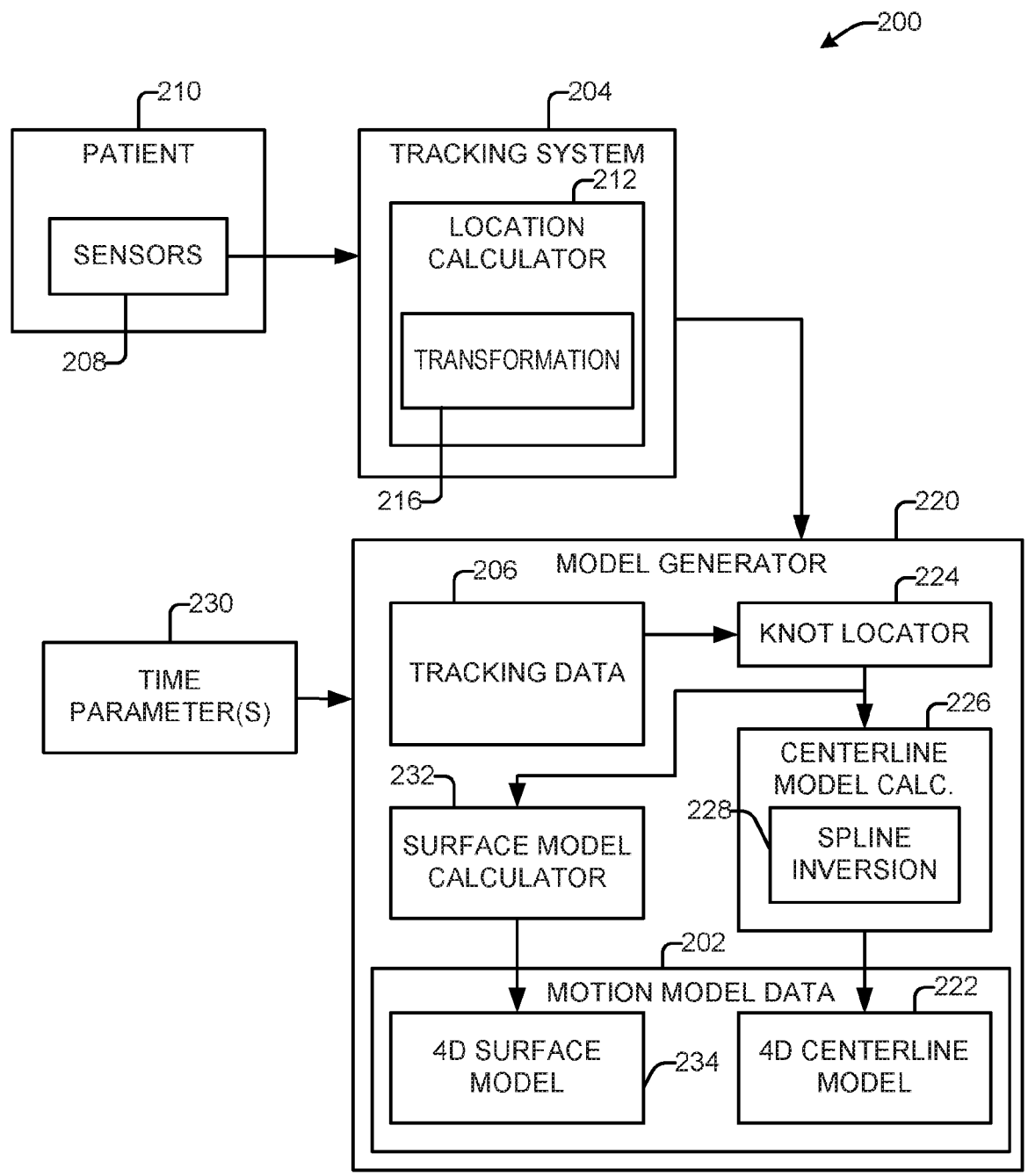
FIG. 2 depicts an example of block diagram of an anatomical behavior characterization system.

As a further example, FIG. 2 depicts an example of block diagram of system 200 to generate a parametric motion model 202 that characterizes the behavior of an anatomical structure of a patient 210 over time (e.g., a 4D spatio-temporal model). As disclosed herein, the motion model 202 may be used to visualize motion of the anatomical structure over time according to one or more temporal parameters that may be used to index through the model 202. In the examples disclosed herein, the anatomical structure may include tubular tissue that includes a lumen having a longitudinal centerline extending through the lumen and a circular sidewall around the centerline. Examples of such tubular tissue includes one or more endovascular structures (e.g., arteries or veins), part of a gastrointestinal tract, part of a respiratory tract or part of a reproductive tract.

The system 200 includes a tracking system 204, which can be the same as tracking system 110 disclosed with respect to FIG. 1. The tracking system 204 thus provides tracking data 206 that describes the position and/or orientation of one or more sensors 208 in a tracking coordinate system in the absence of requiring ionizing radiation. Each sensor 208 may be positioned invasively (e.g., via a low or minimally invasive procedure) within the anatomical structure. As used herein, non-ionizing radiation can refer to any type of electromagnetic radiation that does not carry enough energy per quantum to ionize atoms or molecules—that is, to completely remove an electron from an atom or molecule. Instead of producing charged ions when passing through matter, the electromagnetic radiation provided by the tracking system can have sufficient energy only for excitation, the movement of an electron to a higher energy state. Other types of tracking systems, such as ultrasonic sensors or the like, can also be employed to provide the tracking data 206. The tracking data 206 can include a position and/or orientation in a 3D coordinate system (e.g., a 3D vector) for each sensor 208 that can be detected by the tracking system 204.

For the example of an EM tracking system 204, a location calculator 212 that computes a three-dimensional position and/or orientation for each sensor 208 based on sensor signals from each respective sensor. For instance, the sensor signals are induced in each sensor 208 response to an interrogation field from the tracking system 204 (e.g., a varying magnetic field produced by a field generator). The location calculator 212 may implement a transformation 216 to convert the sensor signals into a corresponding vector that defines the position and orientation of each sensor. For instance, the transformation 216 is applied to the digitized sensors signals to calculate a 3D position and orientation of each sensor relative to an origin residing in a coordinate system of the tracking system according to the spatial volume where the interrogation field is provided. The tracking system 204 may provide tracking data with an output sample rate to enable a model generator 220 to utilize 4D real time positioning information for each sensor for constructing the 4D motion model for the anatomical structure of the patient 210 in real time as the tracking data is generated.

The model generator 220 is configured to generate motion model data 206 that represents the spatial behavior of the anatomical structure over time, including changes in geometry. The model generator may be implemented as machine readable instructions stored in one or more storage media, which when executed by a processor (e.g., of a computing device 112 or 1200) perform corresponding functions and methods, as disclosed herein. The model generator 220 thus executes instructions that compute the model data 206 based on the tracking data 206 for a plurality of time instances. The model generator 220 may access the tracking data 206 that is generated by the tracking system 204 via an application program interface (API), for example. The instructions and corresponding calculations implemented by the model generator to provide the motion model 202 will vary depending on the locations of the sensors 208 relative to the centerline or interior wall of the anatomical structure and the number of sensors.

Figure 4:
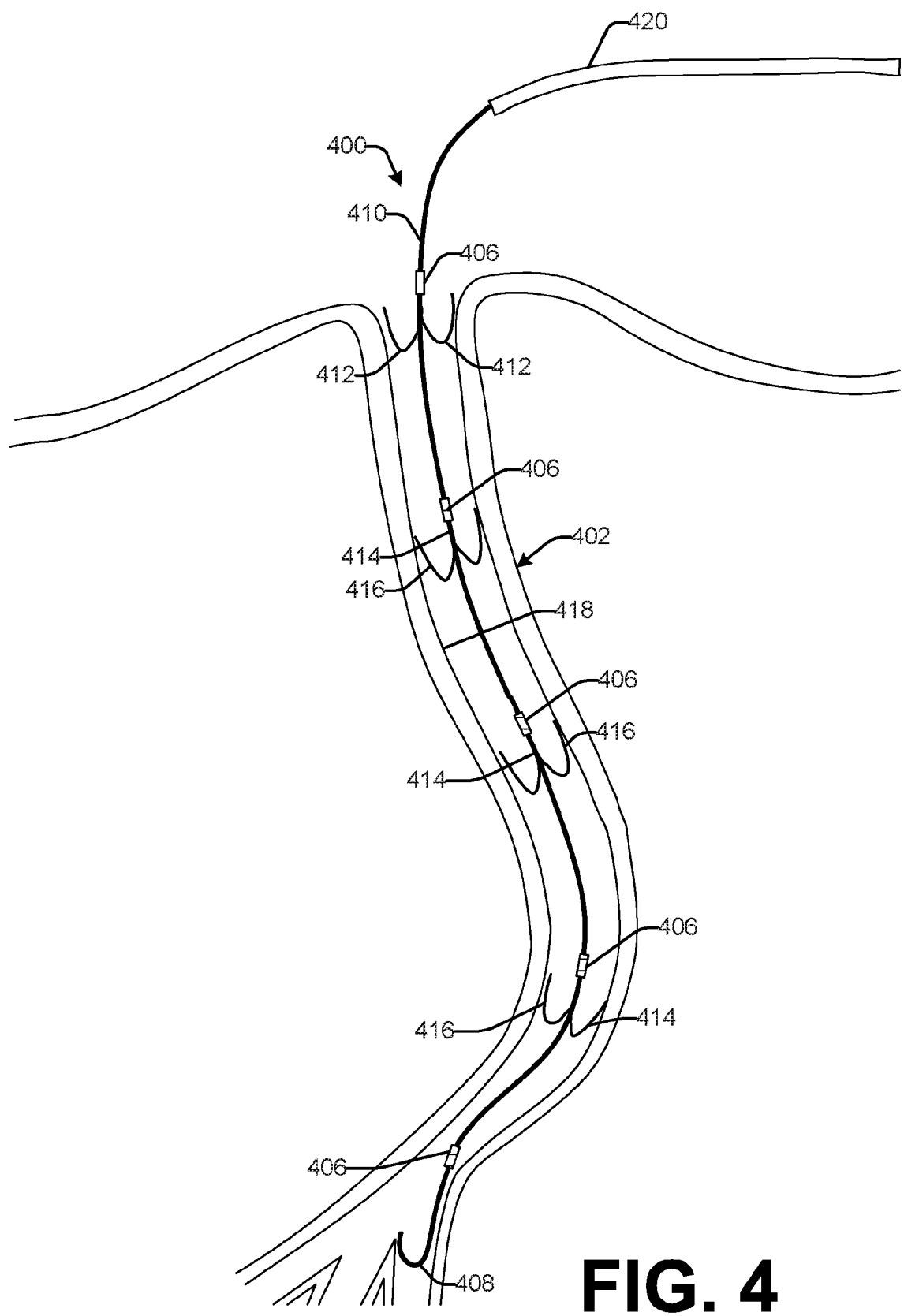
FIG. 4 depicts an example of an apparatus positioned within an anatomical structure for characterizing behavior of the anatomical structure.

In examples where the tracking data 206 is generated from a plurality of sensors positioned along a centerline of a portion of the anatomical structure (e.g., a tubular structure having a lumen, such as shown in FIG. 4), the model generator 220 can utilize the sensor locations (e.g., 3D position and orientation) to compute a 4D centerline model 222. For example, the model generator 220 includes a knot locator function 224 that determines a series of geometric knots along the centerline of the structure according to sensor positions provided by tracking data 206 for each sample time (a time instance) in one or more time intervals. In some examples, the knot locator 222 may interpolate between sensor locations, such as a geometric mean of adjacent sensor locations, to provide interpolated locations that can provide additional geometric knots for centerline locations in each respective time instance. The knot locator 222 can store the 3D locations of each knot for each time instance of one or more time intervals (e.g., in a two-dimensional (2D) array, where each row includes a series of knot locations for a respective time).

A centerline model calculator 224 implements spline inversion 226 to generate corresponding spline interpolants, which parameterize the centerline (e.g., as a lofted basis or B-spline) for each time instance. For example, the spline interpolants can represent the geometry of the centerline as B-splines based on one or more free parameters, such as corresponding to location of geometric knots along the centerline and control points specifying curvature for each respective geometric knot. The centerline model calculator 224 may generate the centerline model 224 as a time-series sequence of such splines indexed according to one or more time parameters 230. For example, a time parameter may be gated to a periodic anatomic function, such as a cardiac cycle (e.g., from an EKG) or a respiratory cycle (e.g., from a respiratory sensor belt). In some examples, more than one time index may be applied to parameterize the centerline over time. For instance, one 4D model can be generated to represent the geometry of the centerline according to a first periodic anatomical function (e.g., cardiac cycle) and another 4D model can be generated to represent the geometry according to second periodic anatomic function (respiratory cycle). Both first and second models thus may represent changes in spatial behavior computed by spline inversion from the same geometric knots collected over time, but the different models include different temporal parameters used to index through centerline geometry (e.g., during spline evaluation) to visualize motion of the structure gated to the respective anatomic function over time. In some examples, such first and second models may be stored as a single 4D model with a variable parameter that can be set to select the temporal parameter in response to an input (e.g., a user or machine initiated input).

The model generator 220 may also include a surface model calculator 232 configured to generate a corresponding 4D surface model 234. For example, the surface model calculator may employ the knot locations and spatial information at each knot (e.g., a diameter) to provide a corresponding parametric model for the centerline. The parameters can include a free parameter a tangential free parameter and temporal parameter. The free parameter, for example, defines a radius or diameter at each of the knots and the temporal parameters are used to index the surface model over time, which can be the same temporal parameter(s) 230 as used in the 4D centerline model 222. Thus, a spline evaluation function can construct a graphical representation of the surface by lofting between circular boundaries (e.g., circles, ellipses or other geometric shapes) defined at geometric knots along the centerline, as indexed in time by the temporal parameter. Thus, the 4D centerline model 224 thus may be computed as a function of one or more free parameters, representing geometry of the structure (e.g., centerline and/or surface geometry) in each time instance, and a temporal parameter (a time stamp) that is used to index the free parameters over time, which may be gated to an anatomical periodic function.

In examples where the tracking data 206 is generated from a plurality of sensors positioned along an interior sidewall of the anatomical structure (see, e.g., FIG. 5), the model generator 220 can utilize the sensor locations (e.g., 3D position and orientation) to compute the surface model 234 and the centerline model 222. The resulting models 222 and 234 may be similarly derived from identified geometric knot locations, as explained above. However, knot locator 224 derives spatial position of the geometric knots along the centerline from the geometry of the lumen provided by the sensors 208. For example, the knot locator 224 computes the geometric knot location as a geometric mean of sensor locations at each sensor station. The remaining computations by the model generator (e.g., by calculators 226 and 232) may be performed in the same manner described in the preceding example.

As disclosed herein, the motion model data may be used to generate a graphical representation of the behavior of the anatomical structure (or a portion thereof for which the model was generated). As one example, the motion of the model may be visualized by overlaying a 4D rendering of the model on a graphical image. As another example, the motion model data may be combined (e.g., registered) with a static parametric model such to provide deformation parameters to enable changes in the geometry to be visualized over time.

Figure 3:
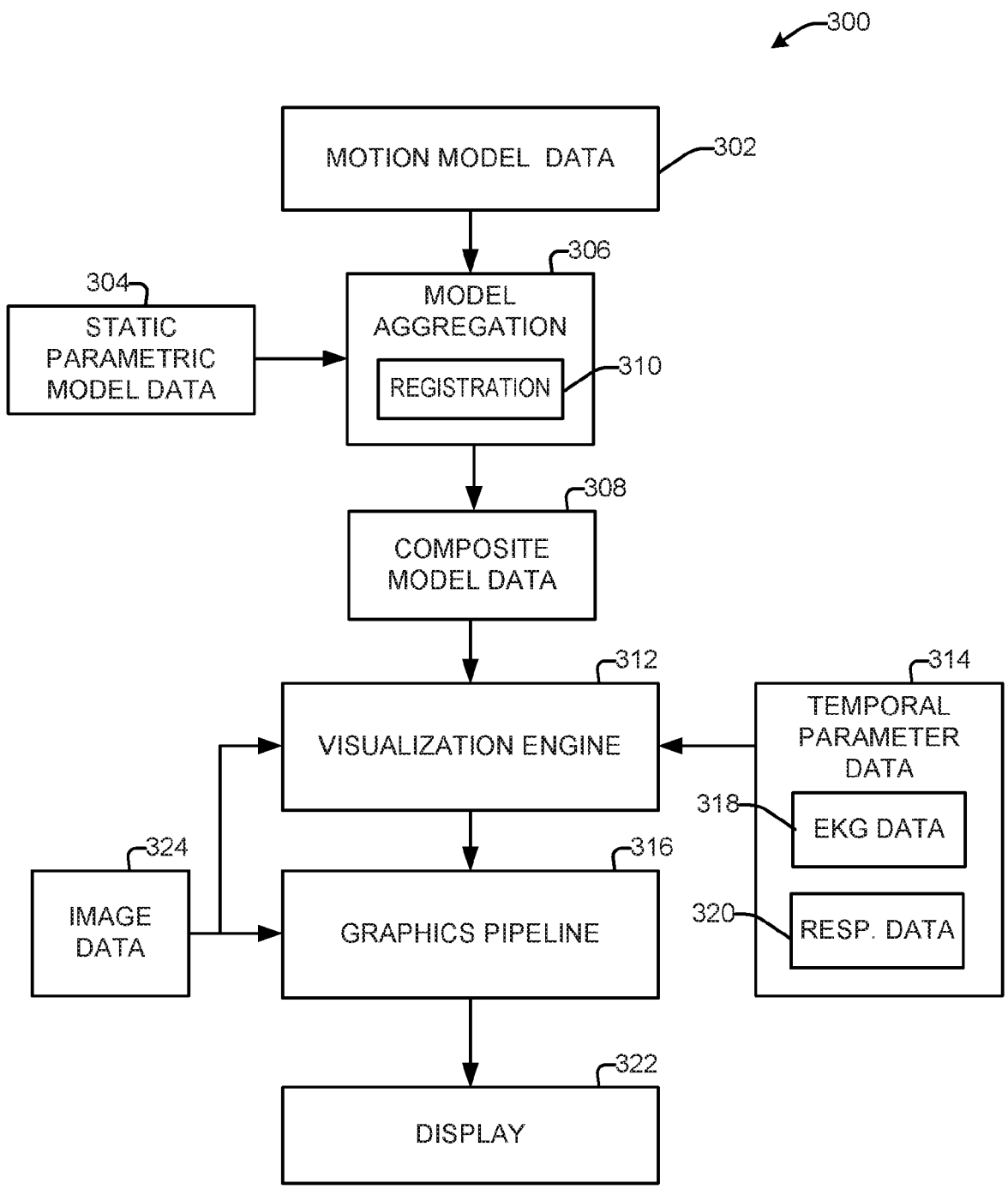
FIG. 3 depicts an example of block diagram of a system to visualize anatomical behavior of an anatomical structure.

As a further example, FIG. 3 depicts an example of a system 300 to visualize anatomical behavior of an anatomical structure. In this example, the system generates the visualization based on motion model data 302 and static model data 304. The motion model data 302 can be stored in memory as the motion model 202 of FIG. 2 (e.g., the surface and centerline models 222 and 234). Thus, the motion model 302 may represent a movement of the anatomical structure over time, such as indexed according to temporal parameter data, for a portion of structure from which the sensor data was acquired. The static model data for example includes one or more free parameters that estimate geometry of the anatomical structure. For example, the free parameter may correspond to a linear free parameter that defines a shape of the centerline of the elongated, tubular anatomical structure that remains fixed over. Alternatively or additionally, the free parameter may correspond to a tangential free parameter that defines a cross-sectional shape of the anatomical structure that also remains fixed. The static model data 304 may be generated in a different process, such as during an offline process, based on 3D image data for the anatomical structure. Since the model 304 is generated from image data, the number of geometric knots and resulting resolution of the static model may be significantly higher than the model generated from the tracking data.

As one example, the model 304 may be generated from image data as disclosed in U.S. Pat. No. 9,047,685, entitled AUTOMATED CENTERLINE EXTRACTION METHOD AND GENERATION OF CORRESPONDING ANALYTICAL EXPRESSION AND USE THEREOF, which is incorporated herein by reference. Another example of generating an implicit model for tubular anatomical structures is disclosed in Analytical centerline extraction and surface fitting using CT scans for aortic aneurysm repair, Goel, Vikash R, Master's Thesis, Cornell University (2005), which is incorporated herein by reference. Other approaches for generating the parametric model 304 can also be utilized. The parametric model for a tubular anatomical structure can be implemented as a lofted basis (b-) spline that includes control points along the centerline and respective control points to define the curvature of the centerline. The parametric model also may include a corresponding surface model, such as by lofting circles between geometric knots along its centerline according to the diameter at such knots (e.g., determined from the image data).

The system 300 includes a model aggregation method (e.g., instructions executable by one or more processors) to combine the motion model 302 and the static model 304 and thereby generate composite model data 306. For example, the model aggregation method includes a registration function 310 to align the motion model 302 with the static model 304. The registration function 310 may utilize a registration matrix to convert the models into a common coordinate system, which may be the coordinate system of the tracking system, a coordinate system of image space from which the static model is generated or another common spatial coordinate system. In this way, the model aggregation provides composite model data in which the motion model may provide deformation parameters for corresponding geometry in the static model, which can be used to show anatomical behavior changes over time as indexed by a temporal parameter 314.

As an example, the registration function 310 may employ a registration engine to co-register the models, such as disclosed in U.S. Patent Publication No. 20140276002, entitled METHOD AND SYSTEM TO FACILITATE INTRAOPERATIVE POSITIONING AND GUIDANCE, which is incorporated herein by reference in its entirety. As another example, the registration function 310 may utilize the location of one or more anatomical or other landmarks specified in each of the models, such as may be specified automatically or in response to a user input (e.g., clicking a pointing device on a common location in graphical version of each model 302 and 304).

The system also includes a visualization engine 312 that utilizes the composite model data 308 to generate input graphical data to a graphics pipeline 316. For example, the visualization engine 312 provides the input graphical data in the form of primitives corresponding to the composite model as indexed by temporal parameter data 314. The graphics pipeline renders a graphical representation of the anatomical structure that is supplied to a display 322.

As an example, the visualization engine employs an evaluation function (e.g., a periodic B-spline evaluation) that evaluates the composite model 308 to provide a series of geometric knots. The series of geometric knots (or a portion thereof) may vary depending on the value of the temporal parameter. For example, a corresponding portion of the anatomical structure that includes deformation model parameters from the motion model data 302 varies spatially as a function of and is indexed by the temporal parameter 314. Other portions of the anatomical structure characterized by the static model data 304 may remain fixed over time and thus not change based on the temporal parameter data. For the example of a tubular structure, for example, the B-spline evaluation thus interpolates between the positions of geometric knots to generate a graphical representation of the centerline that includes one or more portions that change over time (e.g., as described by the motion model for each time index). Similarly, the evaluation function may also construct a corresponding surface model for the tubular structure by lofting between circles disposed about the centerline for each time index.

In some examples, the temporal parameter data 314, which the visualization engine utilizes to index through the composite model data 308, is gated to a cyclic anatomical function. The anatomical function may be received from a sensor in real-time (or near real time) and utilized by the visualization engine 312 as temporal parameter data to index through the time sequence of models to provide gating in response to a sensed anatomical function. The visualization engine thus may provide the inputs to the graphics pipeline 316 in response to the temporal parameter data 314. The temporal parameter data may be a sequence of free flowing time instances, such as according to a sample rate of the tracking system.

In other examples of such temporal parameter data may be correlated with a phase of an anatomical function. For example, the phase of the anatomical function being determine based on input signals corresponding to the anatomical function, such as EKG data 318 and/or respiratory data 320. In systems that receive two more types of temporal data 318 and 320 for indexing the model 308, a user may employ a user interface (e.g., graphical user interface) to provide a user input selecting one of the types of function for gating the model. As mentioned, different motion models may be generated for each type of anatomical function to which the motion model may be gated, which can be reflected in the composite model and selected in response to the user input. The selected type of gating thus determines which motion model data will be utilized in the context of the composite model and, in turn, indexed according to the corresponding type of temporal parameter data. In some examples, different composite models may be constructed by the model aggregation for each type of possible gating that may be implemented by the system 300. Alternatively, the selected type of temporal parameter can be applied to the motion model for indexing the model through the corresponding sequence of time instances.

As a further example, the motion model data may be computed in a just-in-time manner (e.g., approximating real time with any delays due to processing time). For example, the model aggregation applies the motion model data that is generated for a given time instance (in real time) to the static model 304 to re-compute the composite model data 308 for each time instance. In this way the composite model data may continually change according to the spatial behavior that is reflected in the motion model.

In some examples, additional tracking data may be acquired while another device is implanted, temporarily or permanently, within the anatomical structure. The additional tracking data may reflect the position of the other device that is being implanted. In this example, a difference between the motion models generated before and after the other device is implanted may be determined. The corresponding difference thus may be integrated into the composite model to visualize changes in the model on the display, for example by simultaneously rendering both models using different colors. This may allow medical staff to appreciate the effect the implanted device may have on the behavior of the anatomical structure, and to infer clinical significance.

FIG. 4 depicts an example of an apparatus 400 within an anatomical structure 402 for characterizing behavior of the anatomical structure that changes over time. For example, the apparatus 400 is an endovascular device that includes an elongated, pliant guidewire 404 that includes a plurality of sensors 406 distributed along the length of the guidewire from a distal end 408 to an intermediate location 410 spaced from the distal end. The locations where sensors 406 are located may be referred to as stations. In examples where the tracking system is an EM tracking system, the sensors 406 may be implemented as sensor coils that provide respective sensor signals, such as disclosed herein.

In the example of FIG. 4, the guidewire 404 includes legs 412 attached to the guidewire at or adjacent to each of the sensor stations. The legs 412 at each station are biased to self-expand radially outwardly from a first end 414, which is attached to the guidewire 404, and terminate in a respective distal end 416 that engages contact locations along an interior wall 418 of the anatomical structure. For example, as shown, the distal end 416 may be curved (or otherwise configured) as to rest against the interior surface of the wall 418 without penetrating into the tissue. In an example, there may be one set of legs 412 to position each of the sensors 406. The number of legs and sensors 406 may vary depending on the stiffness of the guidewire 404 and/or the length of the wall 418 that is being characterized, as disclosed herein.

By way of example, upon being deployed from a sheath (e.g., catheter) 420 within the wall 418, the legs deflect radially outwardly and engage the adjacent wall. In an example that includes a pair of diametrically opposed legs 412 at each station, the legs 412, when deployed, retain the guidewire 404 at an intermediate distance between the distal ends 416 thereof, such that the length of the guidewire (at least the portion extending between 408 and 410) including sensors 406 are held centered between the opposing surfaces of the wall 418. In other examples, more than two (e.g., 3, 4 or more) legs may extend from the guidewire 404 to hold the guidewire and each of sensors along the centerline of the vessel wall 418. After the measurements have been made over a period of time deemed sufficient to characterize the behavior of the structure 402 over time, the sheath may be advanced over the legs and guidewire and then removed from the structure 402. In other examples, the guidewire may be moved to one or more different locations within the structure 402 to obtain additional measurements for characterizing different portions of the structure over time.

Figure 5:
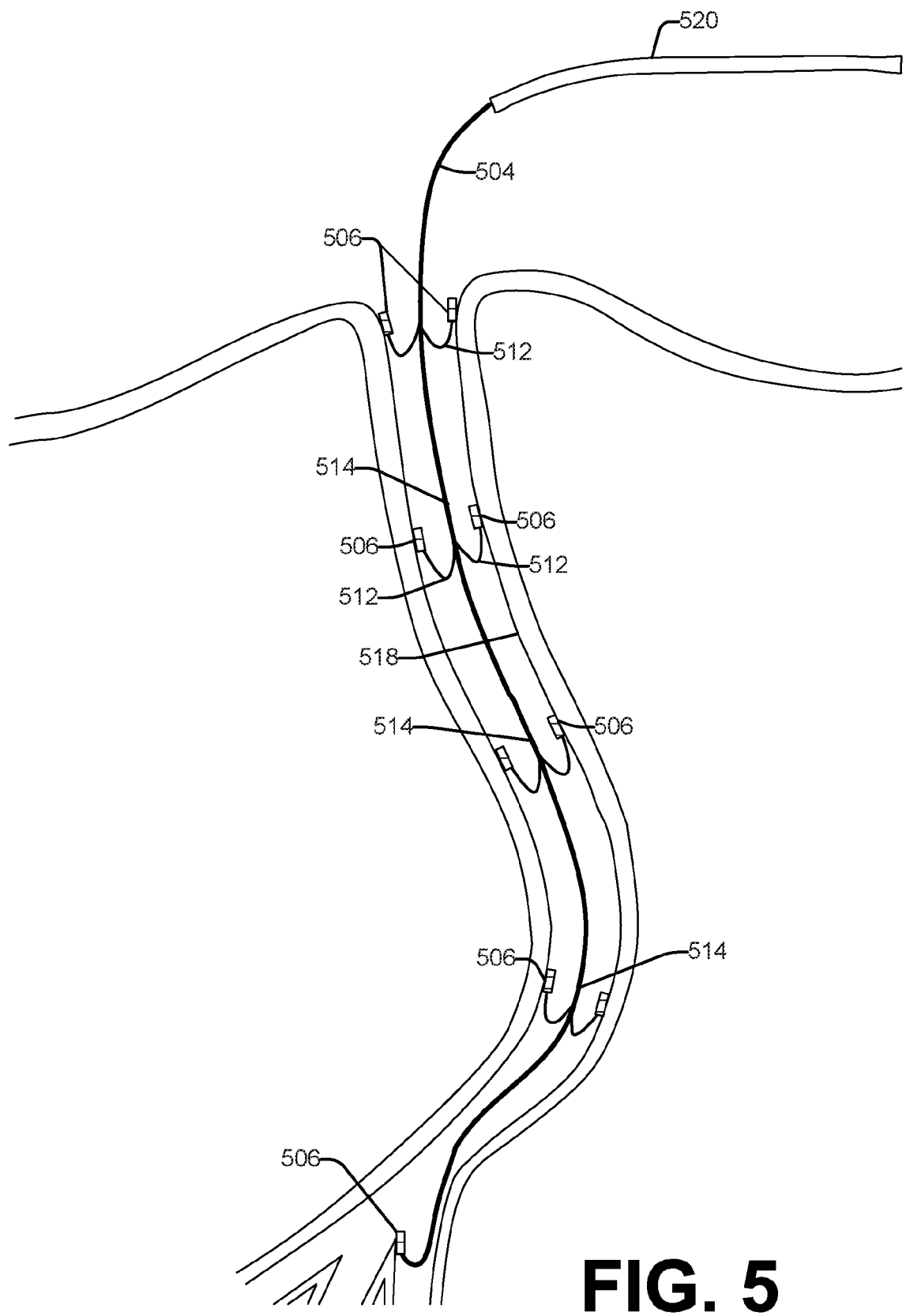
FIG. 5 depicts an example of another apparatus positioned within an anatomical structure for characterizing behavior of the anatomical structure based on sensors contacting a vessel wall.

FIG. 5 depicts an example of another apparatus 500 positioned within an anatomical structure for characterizing behavior of the anatomical structure based on sensors 516 contacting an interior of a vessel wall 518. For sake of simplicity of explanation, in the example of FIG. 5, identical reference numbers, increased by adding 100, are used to identify features previously introduced in FIG. 4. Reference thus may be made back to FIG. 4 for additional information about such features. Briefly stated, the example of FIG. 5 is similar to FIG. 4 except that the legs 512 include sensors 516 at their distal ends 514 that engage contact locations along the interior wall 518 of the anatomical structure 502. In the deployed condition, for example, a pair of diametrically opposed legs thus support respective sensors in a diametrically opposed position such that a distance between such sensor pair corresponds to a diameter of the wall 518 at such location.

As a further example, the diameter each station further may be used (e.g., by anatomical characterization 116) to compute a parametric surface for the vessel wall 518 by lofting circles at each sensor station (e.g., via spline interpolation and fitting). The corresponding parametric surface model thus may be stored in memory for each time instance such as indexed by a cyclic anatomical function (e.g., EKG and/or respiratory cycles). Additionally, by determining the location of sensors over a plurality of time samples during a time interval, the location of the center of the wall 518 may be determined as the geometric mean of the pair of sensor locations at each time sample.

Figure 6:
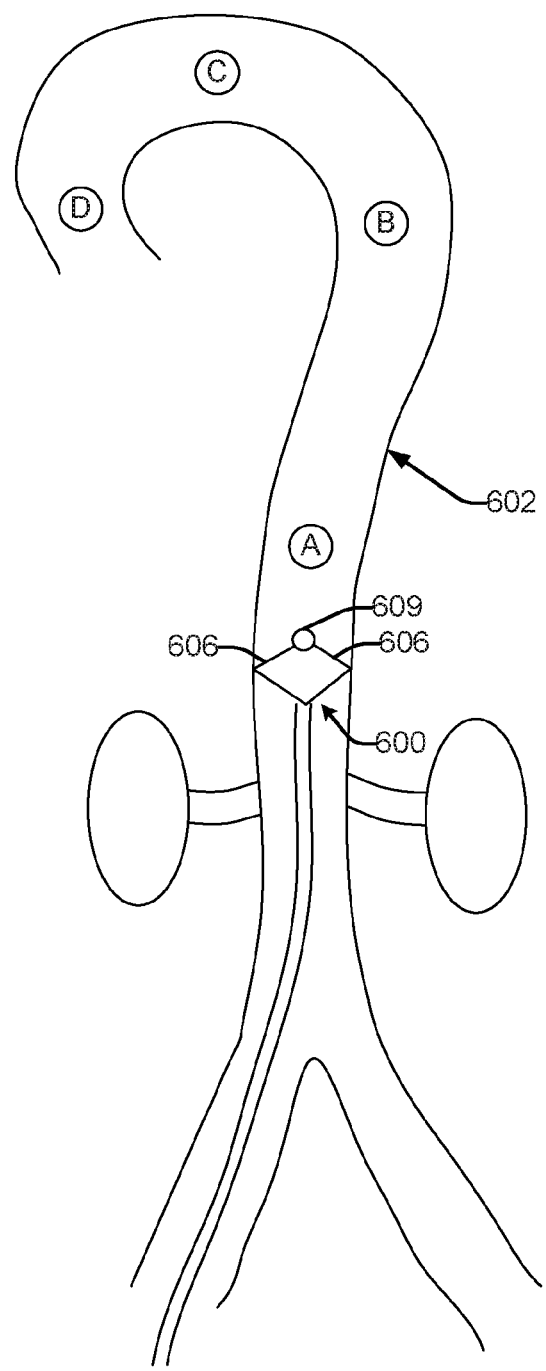
FIG. 6 depicts an example of another apparatus positioned within an anatomical structure for characterizing behavior of the anatomical structure.

FIG. 6 depicts an example of another apparatus 600 within an anatomical structure for characterizing behavior of the anatomical structure. In this example, the apparatus 600 is positioned within the thoracic aorta 602. Additionally for sake of clarity, the apparatus is shown with a single sensor 604. Legs 606 extending from the guidewire 608 are self-biased, such that when deployed from the sheath they contact the adjacent sidewall of the aorta 602 and support the sensor 604 at a geometric center of the aorta. The apparatus 600 may be repositioned to a plurality of upper aortic sections, demonstrated at A, B, C and D, to collect position data over time for each such section. In this way, the system and methods disclosed herein can be employed the collected position data over time to characterize motion of the upper as well as lower aortic sections. By indexing the data collected from the different sections to one or more common anatomical functions, such as cardiac or respiratory cycles, the data can be aggregated to generate a visualization describing the motion for the set of aortic sections over time. The number of sections may vary depending on the number of sensors distributed along the length of the guidewire.

Figure 7:
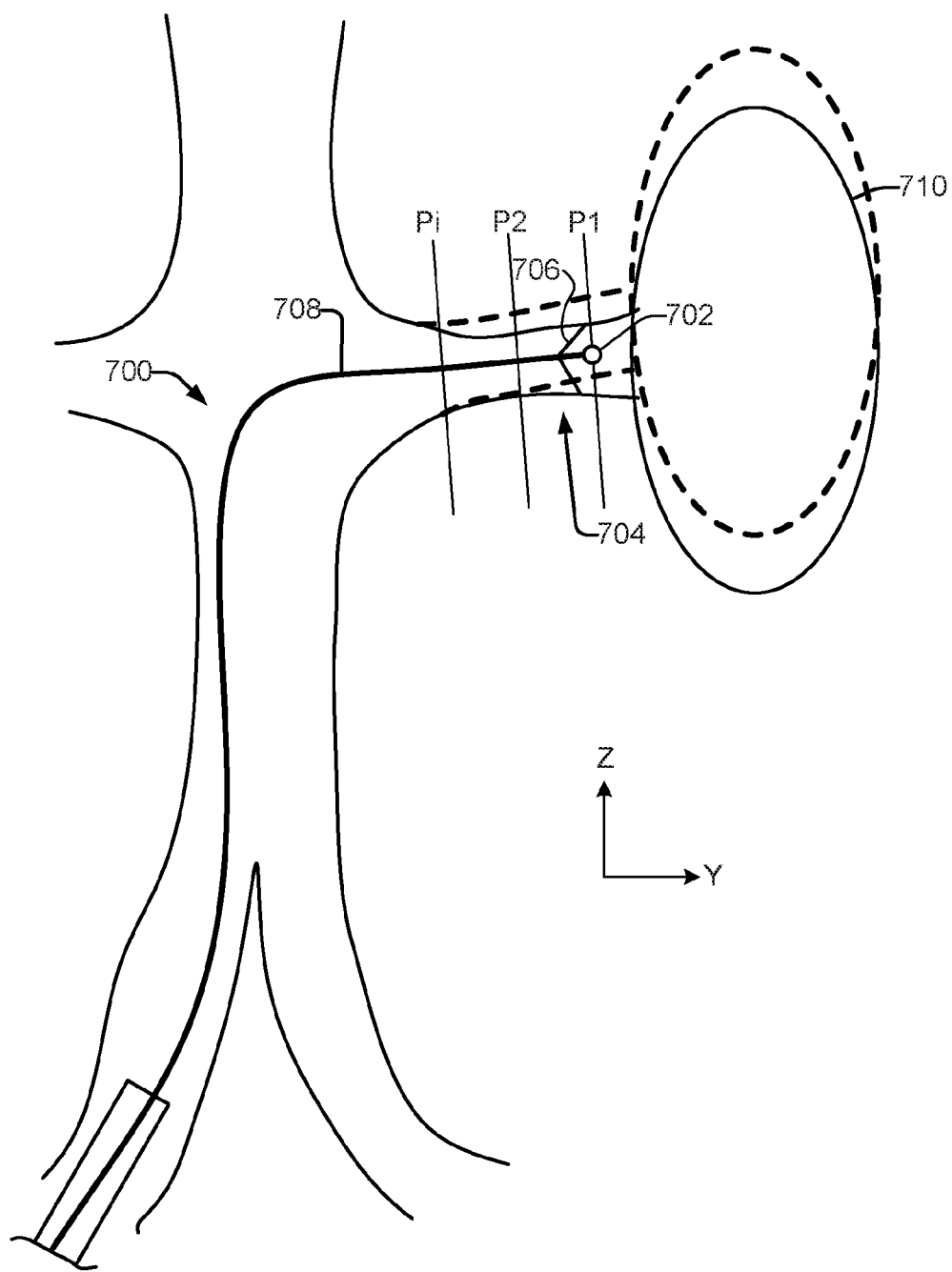
FIG. 7 depicts an example of an apparatus positioned within another anatomical structure for characterizing behavior of the anatomical structure.

FIG. 7 depicts an example of an apparatus 700 within another anatomical structure for characterizing behavior of the anatomical structure. In the example of FIG. 7, the apparatus includes a sensor 702 positioned within a patient's renal artery 704. The apparatus includes legs 706 that extend outwardly from a guidewire 708 to fix the position of the sensor 702 within the renal artery 704. While fixed within the vasculature, position data may be collected over time along with anatomical function data, such as respiratory cycle data. As mentioned, the respiratory cycle data may be used to index the position data over time. For example, the motion of the renal artery 704 and kidney 710 may shift between positions shown in dashed and solid lines, which motion may be captured by the data collected over time and indexed by the respiratory cycle data that is collected simultaneously with the position data. Additionally, the sensor 702 may be moved via the guidewire 708 to each of the positions P1, P2, Pi (where i denotes the number of sensing stations) where the sensor is positioned (e.g., at each position Pi) along the renal artery to generate tracking data during a corresponding time interval, which may include one or a plurality of respiratory cycles. In other examples, a sensing device that includes a plurality of sensors distributed along the distal end of the guidewire may be positioned within the artery 704 to provide corresponding tracking data. Sensor position tracking data at each location, which is generated by a tracking system, further may be aggregated to characterize motion of the entire or a portion of the renal artery 704 with respect to (as indexed by) a respiratory cycle. The aggregation of tracking data acquired for multiple sensor stations over an anatomical cycle may include aligning and synchronizing the position and/orientation data with respect to the anatomical cycle to enable the position of different portions of the renal artery (or other anatomical structure) to be indexed by a common time cycle, such as the respiratory cycle.

In view of the foregoing structural and functional features described above, methods in accordance with various aspects of the invention will be better appreciated with reference to FIGS. 8-11. While, for purposes of simplicity of explanation, the methods are shown and described as executing serially, it is to be understood and appreciated that the methods are not limited by the illustrated order, as some aspects could, in other examples, occur in different orders and/or concurrently from that shown and described herein. Moreover, not all illustrated features may be required to implement a method. Additionally, the methods of FIGS. 8, 10 and 11 may be implemented as machine-readable instructions which, when executed by a processing device, perform or cause to be performed the respective methods.

Figure 8:
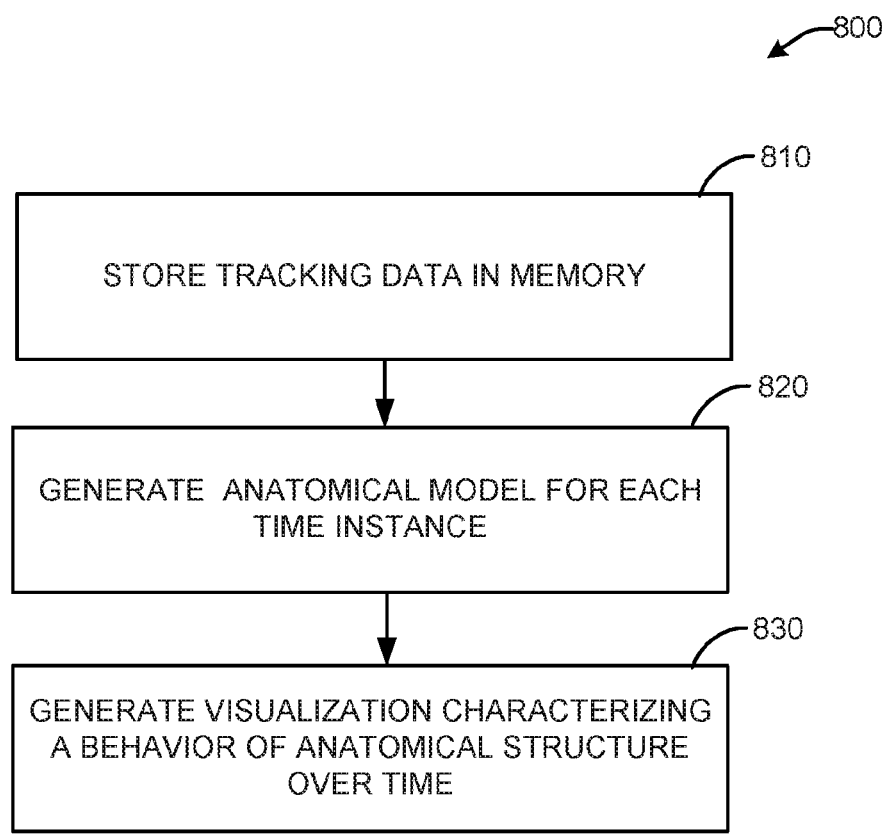
FIG. 8 is a flow diagram depicting an example method for characterizing a behavior of an anatomical structure.

FIG. 8 depicts an example method 800 for characterizing a behavior of an anatomical structure. The method 800 can be implemented, for example, by a computing device (e.g., the computing device 112, as illustrated in FIG. 1 or as otherwise described herein). At 810, tracking data is stored in memory. The tracking data can be generated by a tracking system (e.g., tracking system 110 or 204) to represent the position and/or orientation of one or more sensors in a coordinate system during a change in spatial behavior of an anatomical structure of a patient that occurs over time. Since the sensors are fixed relative to the anatomical structure, the tracking that is provided at 810 data can represent the position of corresponding anatomy (where affixed) for a sequence of time samples acquired over one or more time intervals.

At 820, a motion model is generated for each instance (time sample) of the time interval. As disclosed herein, the motion model is a 4D parametric model (e.g., a time-ordered sequence of 3D parametric models) describing motion of the anatomical structure over time. The motion model is stored in memory (e.g., volatile and/or non-volatile memory). For the example of a tubular structure having a lumen (e.g., a vessel, gastro-intestinal tract or respiratory tract), the parametric motion model at each instance may include parameters (e.g., geometric knots and control points) representing a centerline of the lumen as well as parameters (e.g., diameter at locations along the centerline) representing surface geometry of the lumen.

At 830, a visualization characterizing the behavior of the anatomical structure over time is generated. As disclosed herein, the motion model can characterize motion of a portion of the anatomical structure according to the anatomical locations where the sensors are fixed for providing the tracking data at 810. In some examples, the visualization includes a graphical rendering of the motion model overlayed on an image of the patient's anatomical structure (e.g, acquired pre- or intraoperatively). Additionally or alternatively, the visualization may be generated based on the motion model providing deformation parameters over time for a portion of the anatomical structure that is rendered from another (separately-generated) parametric model. For instance the other separately-generated model may be generated from image data (acquired for the patient from pre-procedure imaging), such as disclosed herein.

In some examples, the motion model may be generated intraoperatively and the visualization rendered in real-time to graphically represent and characterize spatial changes in the anatomical structure over time. In addition or as an alternative, this may include generating the motion model while another device or object (e.g., catheter and/or stent) is being implanted or moved within the anatomical structure. As another example, the visualization generated at 830 can include a graphical representation derived from a spatial difference between motion models generated for the anatomical structure at different time intervals. For instance, the visualization is generated to characterize changes in the behavior of the anatomical structure between the first and second time intervals. The changes in behavior may be from naturally occurring biological changes in the patient and/or due to placement or removal of one or more other objects in the anatomical structure. In this way, differences between the motion model with and without the other device or object may provide additional insight on the effect of such device or object on the anatomy as it is positioned or moved.

Figure 9:
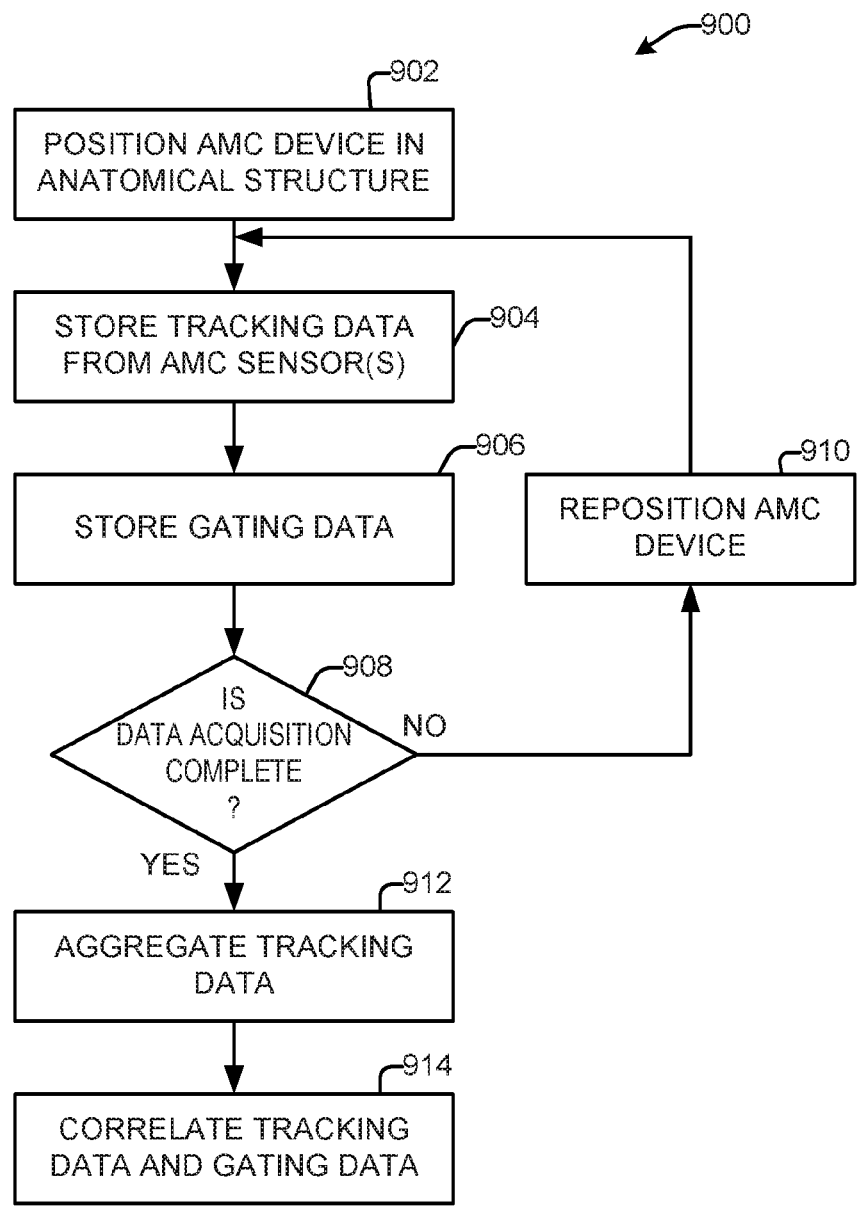
FIG. 9 is a flow diagram depicting an example method for acquiring tracking and temporal data.

FIG. 9 is a flow diagram depicting an example of a method to acquire tracking data that can be utilized to characterize motion of an anatomical structure of a patient over time. The method 900 is utilized in conjunction with an invasive procedure such as may be a low-invasive or minimally-invasive procedure in which a tracking object having one or more sensors is inserted into the patient's body. As an example, one or more sensors may be attached to an object or instrument that is inserted and fixed, temporarily, with respect to an anatomical structure of interest. As disclosed herein, the anatomical structure of interest corresponds to a portion of anatomy that is subject to movement over time.

In some examples, the movement may exhibit a cyclic or periodic behavior relative to one or more other anatomic functions. For example, the cyclic behavior of breathing (e.g., the respiratory cycle) may result in motion of the aorta or renal arteries that varies as a function of the respiratory cycle. Additionally or alternatively, the cardiac cycle may cause the aorta or other anatomical structures to move commensurate with each heart beat. The motion of these and other anatomical structures thus may be captured by a tracking system to provide a corresponding visualization without requiring ionizing radiation.

The method 900 begins at 902 in which an AMC device is positioned in the patient's anatomical structure. For example, the AMC device may be positioned within a lumen of a tubular structure such as an endovascular structure. As disclosed herein, the device can include one or more sensors distributed along a guidewire, on distal ends of legs or other instrument that is positioned in the patient's body. At 904, tracking data from one or more sensors is stored. The tracking data thus can represent the position and/or orientation of each sensor in a 3D coordinate system obtained in the absence of ionizing radiation.

For example, the sensors can be implemented as coils and the tracking data can represent the position and/or orientation of each sensor coil in a coordinate system of the tracking system (e.g., an EM tracking system). The tracking data can include a time stamp that specifies timing information for the tracking data that may be acquired over time interval. The time stamp may be a time stamp generated by the tracking system or a time stamp of the acquisition system or a globally synchronized time stamp, such as UBTMS time.

In some examples, gating data may also be stored at 906. The gating data can describe timing associated with an associated anatomical function of the patient that occurs concurrently with the acquisition of tracking data at 904. For example, the gating data can be acquired or derived from one or more sensors that are attached to the patient during the generation of the tracking data from the AMC sensors. The gating data and the tracking data may have a common time stamp or otherwise be synchronized in time to facilitate synchronization and alignment of such data.

At 908, a determination is made as to whether the data acquisition is complete. If the data acquisition is not complete the method proceeds to 910 in which the AMC device may be repositioned or to acquire additional tracking data for a different location or set of locations in the anatomical structure. Additionally or alternatively, at 910, the AMC device remains at the same location relative to the anatomical structure, and another set of tracking data is acquired for a different condition. The different condition may be the addition of another device in the anatomical structure, application of a therapy or functions that might affect motion of the anatomical function. From 910 the method returns to 904 to repeat the storing of tracking data and gating data for the new position of the sensors.

If the data acquisition is complete at 908 the method proceeds to 912. At 912, the tracking data that was acquired over one or more phases of data acquisition are aggregated together. For example, the tracking data can include more than one continuous time sequence and tracking data for the position and/or orientation of sensors at multiple locations fixed within the anatomical structure. Each set of tracking data thus can represent motion of a corresponding region of the anatomical structure where the sensors reside during the acquisition process.

At 914, the tracking data and gating data (if any) can be correlated. For example, the common time stamp may be used to align the associated tracking data and gating data. In this way the sequence of positions that the anatomical structure changes over time may be time-correlated to a gating anatomical function. The respective tracking data and gating data thus can be stored in memory for further processing such as disclosed herein.

Figure 10:
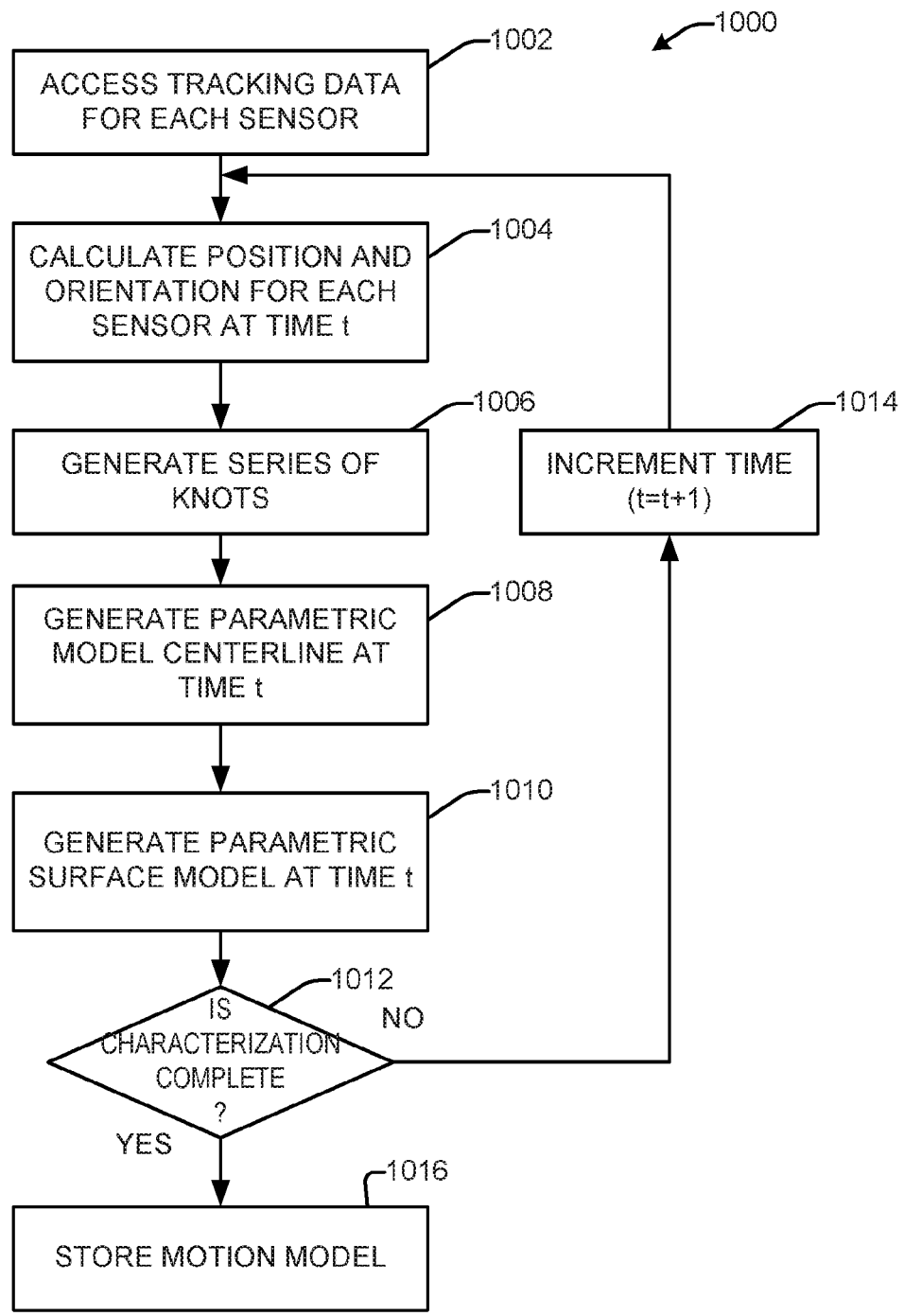
FIG. 10 is a flow diagram depicting another example method for characterizing a behavior of an anatomical structure.

FIG. 10 is a flow diagram depicting an example of a method 1000 that can be utilized to generate a motion model for characterizing the behavior of an anatomical structure over time. The method 1000 begins at 1002 in which the tracking data for each sensor is accessed from memory. The tracking data can be acquired as disclosed with respect to FIG. 9, for example. Thus, the tracking data may represent the position and/or orientation of each of a plurality of sensors that is positioned and fixed relative to an anatomical structure. By fixing the sensors with respect to the anatomical structure the sensors can thus move commensurate with motion of the anatomy over time. The tracking data thus provides information describing a 3D position of the anatomy at sensor locations over a sequence of time instances. At 1004, a position and orientation for each of the plurality of sensors is calculated for a given time instance (t). In some examples, the position and orientation at each time instance can be computed by the tracking system. In other examples, the position and orientation calculated at 1004 at a given time instance may be performed by a computing device that receives a corresponding tracking data from the tracking system, which may include normalizing and scaling the tracking data to a desired format.

At 1006, a series of geometric knots are generated based on the tracking data for the given time instance (t). Each of the knots may correspond to or be derived from the location of each respective sensor defined in the tracking data for the given time instance. For the example where the AMC device is configured to position each of a plurality of sensor stations along a centerline of a tubular structure lumen (see, e.g., FIG. 4), the position of each sensor station may define a geometric knot at 1006. In an example where the AMC device is configured to the position a plurality of sensors on the lumen wall (see, e.g., FIG. 5), geometric knots may be calculated (e.g., a geometric mean) from the sensor locations at each sensor station. Depending upon the distribution of sensors along the length of the AMC device, additional knots may be interpolated between sensor stations axially along the centerline.

At 1008, a parametric centerline model is generated for the given time instance (t). For example, since tracking data for each of the sensor locations and the corresponding knots define the centerline locations at the given time instance, the corresponding parametric model for the centerline can be constructed, such as a B-spline representing the three-dimensional position of each of the geometric knots and control points to define the curvature of the centerline at the given time instance. At 1010, a parametric surface model for the current time instance is generated. The surface model can be generated, for example, based on a diameter of the lumen at each respective geometric knot (at 1006). The diameter may be determined from the image data or from one or more sensors that are part of the AMC wire. In other examples, an estimated constant diameter may be utilized for generating the surface model.

At 1012 a determination is made as to whether the characterization is complete. If the characterization is not complete (NO), the method proceeds to 1014 in which time is incremented. From 1014, the method returns to repeat 1004-1012 to perform the calculations and ultimately generating the model for characterizing the anatomical structure at the next time instance. Thus, by repeating 1004-1014 over a plurality of time instances in a time interval, a sequence of parametric models for the anatomical structure, including centerline and surface models, may be generated. Once the characterization over one or more time intervals has been completed, the method can proceed to 1016 in which the resulting motion model (a 4D parametric model) is stored in memory. In this way, the motion model can represent and be used to characterize changes in behavior of the anatomical structure over time. As disclosed herein, the model can correspond to a portion of the anatomical structure in which the sensors have been positioned during the acquisition over time.

Figure 11:
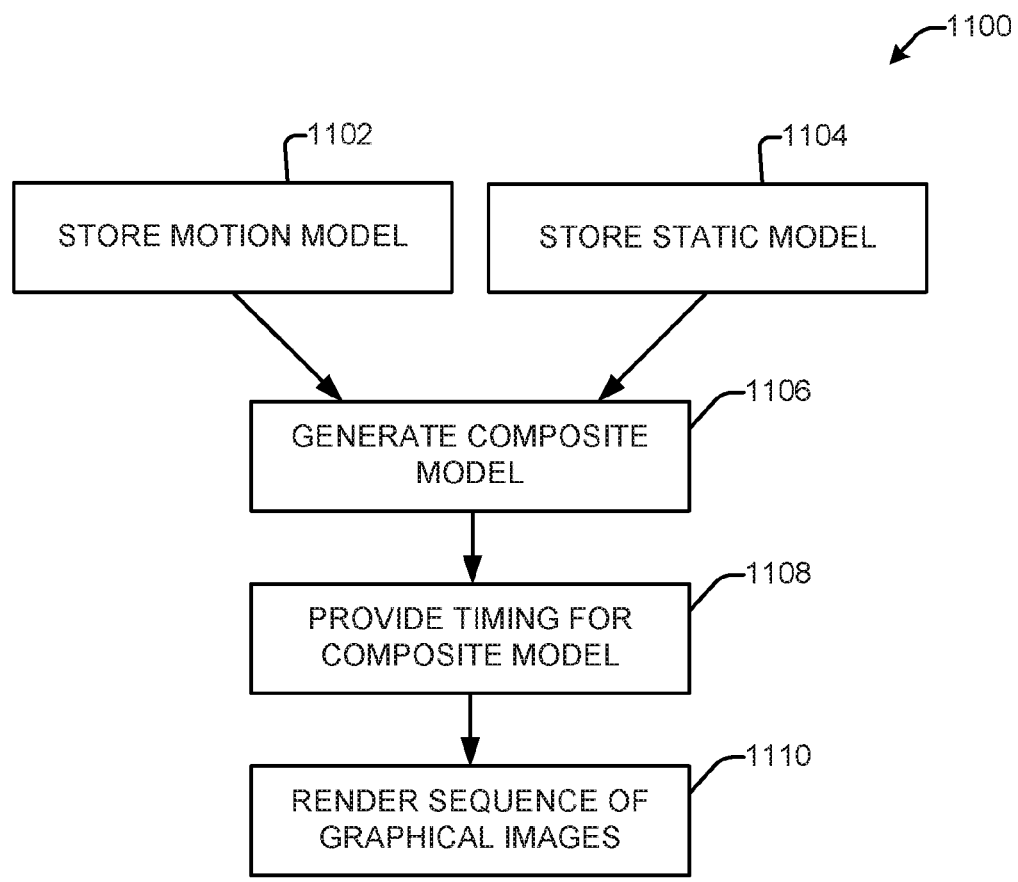
FIG. 11 is a flow diagram depicting yet another example method for characterizing a behavior of an anatomical structure.

FIG. 11 is a flow diagram depicting an example of method 1100 for displaying a graphical representation characterizing motion of an anatomical structure over time. The method 1100 includes storing a motion model (e.g., the motion model generated in FIG. 10) and storing a static model in memory 1104. For example, the static model at 1104 can be constructed based on image data, such as disclosed herein. At 1106, a composite model is generated. The composite model thus combines the motion model and the static model. For example, the motion model can provide deformation parameters for a portion of the static model. The motion model that is in memory at 1102 may be generated before implementing the method 1100 for visualizing the motion of the anatomical structure. In other examples, the motion model that is generated and stored in memory at 1102 in the method 1100 may be generated in real time for each of a plurality of time instances as the tracking data is generated via sensors during an invasive procedure that is implemented concurrently with the method 1100. That is, the methods of FIGS. 9, 10 and 11 may be implemented together as part of a real-time intraoperative procedure.

At 1106 a composite model is generated. The composite model utilizes the motion model for a portion of the anatomical structure of interest (corresponding to the region(s) where tracking data was obtained) and the static model as a baseline for the remaining part of the anatomical structure. The motion model thus may be used to deform a spatially correlated portion of the static model over time. For example, the static parametric model at 1104 may correspond to a high resolution model of the entire anatomical structure, including the branches. In contrast, the motion model may be a lower resolution model derived from geometric knots that are spaced further apart based on the positions of sensors are tracked intraoperatively by the tracking system as disclosed herein. Thus, the composite model will include a time-ordered sequence of deformation parameters that provide a motion model for a portion of the anatomical structure represented by the static parametric model.

At 1108, timing for the composite model is provided. The timing can be a free flow of time (e.g., over one or more time intervals) during which the anatomical model has been generated. The sequence may thus represent a previous (historical or retrospective) time interval during which the tracking data was generated. Alternatively, the timing for the composite model may correspond to a current time (e.g., real time) interval, less nominal processing time utilized for generating the motion model that is stored at 1102. Additionally or alternatively, in some examples, the timing for the composite model at 1108 is correlated with phase of an anatomical function of the patient, such as a respiratory cycle or a cardiac cycle. As disclosed herein, the particular timing that is utilized for the composite model may be selected in response to a user input or otherwise utilize a default timing parameter. At 1110, a corresponding sequence of graphical images is rendered from the composite model according to the timing provided at 1108. In this way a user can visualize on a display (e.g., a monitor or heads up display), motion of one or portions of an anatomical structure over time. As disclosed herein, various parameters of the visualization may be controlled in response to a user input (e.g., enter via a user input device).

Figure 12:
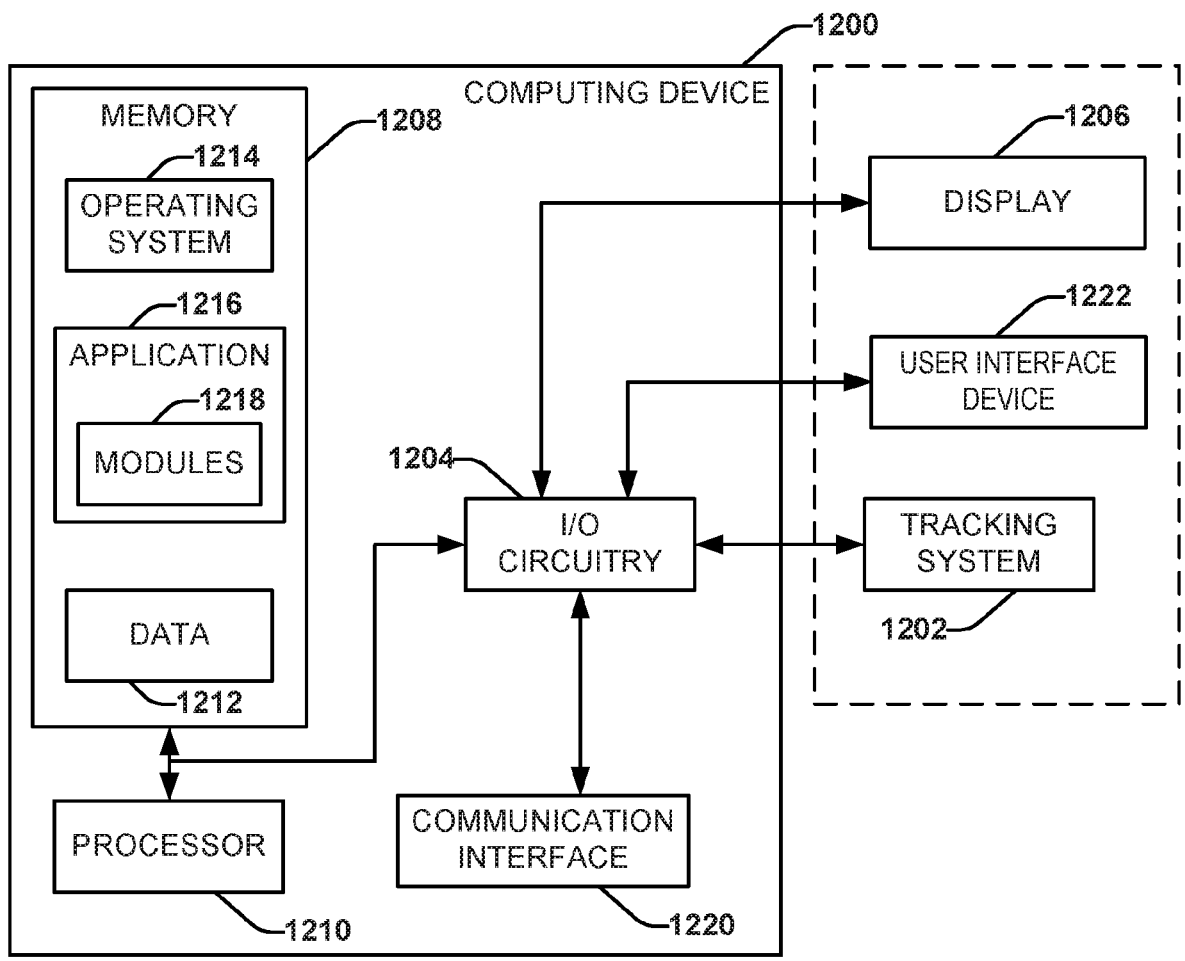
FIG. 12 depicts an example operating environment that includes a computing device.

FIG. 12 depicts an example of an operating environment that includes computing device 1200 (e.g., the computing device 112, as illustrated in FIG. 1) that can communicate with a tracking system 1202 (e.g., the tracking system 112 or 204) via I/O circuitry 1204. The computing device 1200 can also interface with a display device 1206. The display device 1206 is communicatively coupled to the computing device 1200 (e.g., via the I/O circuitry 1204). One or more user interface device 1222 may also be utilized to provide for human-machine interaction. The user interface 1222 may be coupled to the computing device 1200 via the I/O circuitry 1204 or be integrated into the computing device. The computing device 1200 can include one or more computing apparatuses that can include a memory 1210 and a processor 1210. The memory 1208 can be a non-transitory memory that can be configured store machine readable instructions and data 1212.

By way of example, the memory 1208 can store a variety of machine readable instructions and the data 1212, including an operating system 1214, one or more application programs 1216, one or more program modules 1218 associated with at least one of the one or more application programs 1216. The operating system 1214 can be any suitable operating system or combinations of operating systems, which can depend on manufacturer and system to system corresponding to different computer manufacturers. The memory 1208 can be implemented, for example as volatile memory (e.g., RAM), nonvolatile memory (e.g., a hard disk, flash memory, a solid state drive or the like) or combination of both. It is to be understood that the memory 1208 does not require a single fixed memory but the memory 1208 can include one or more non-transitory machine readable memory (e.g., volatile and/or non-volatile memory devices) that can store data and instructions.

The memory 1208 can store data 1212 and/or instructions corresponding to the operating system 1214 and/or the one or more application programs 1216 in a single device or distributed across multiple devices, such as in a network or a cloud computing architecture. In one example, the data 1212 can include tracking data characterizing the 3-D position and/or orientation of each of the one or more EM sensors (e.g., sensors 106) over time supplied by the tracking system 1202.

Additionally or alternatively, the data 1212 can include image data characterizing the patient anatomy. The image data can be acquired by an imaging modality, such as computed tomography (CT), magnetic resonance imaging, multi-plane x-ray or the like, which can be configured to provide a 3-D image of patient anatomy in a coordinate system. The processor 1210 can access the memory 1208 and execute the machine readable instructions (e.g., corresponding to the operating system 1214 and/or the application 1216) to facilitate the performance of operations. For example, the processor 1210 can access the memory 1208 to access the one or more application programs 1216 that implement one or more program modules to generate and utilize one or more anatomical models, such as disclosed herein. For example, the program modules 1218 may execute and/or control functionality disclosed with respect to FIGS. 1, 2 and 3 and methods of FIGS. 8, 10 and 11, such as to generating models and visualizations.

In view of the foregoing, systems and methods disclosed herein enable the anatomical behavior can be evaluated over time without requiring ionizing radiation. This may include determining the effects anatomical functions have on the anatomical structure and/or the effects an implantable object has on the motion of the anatomical structure (e.g., during placement and positioning thereof the object relative to the anatomical structure). The motion data captured prior to placement of the implantable device relative to the anatomical structure can be evaluated relative to the motion data captured after placement of the of the implantable device relative to the anatomical structure.

As another example, systems and methods can characterize motions of the anatomical structure before and after deployment of an implantable device relative to the anatomical structure. This provides an insight into the effects that the implantable device has on the anatomical structure, which can be used to improve. Employing the systems and methods during an endovascular procedure allows medical staff to visualize in real-time the behaviors exhibited by the endovascular structure, for example, intraprocedurally, and understand how such behaviors relates cardiac and respiratory cycles of a patient. This may be done without further exposing the staff or the patient to ionizing radiation.

What have been described above are examples. It is, of course, not possible to describe every conceivable combination of components or methods, but one of ordinary skill in the art will recognize that many further combinations and permutations are possible. Accordingly, the invention is intended to embrace all such alterations, modifications, and variations that fall within the scope of this application, including the appended claims. As used herein, the term "includes" means includes but not limited to, the term "including" means including but not limited to. The term "based on" means based at least in part on. Additionally, where the disclosure or claims recite "a," "an," "a first," or "another" element, or the equivalent thereof, it should be interpreted to include one or more than one such element, neither requiring nor excluding two or more such elements.

What is claimed is:

1. A system to characterize motion of an anatomical structure, comprising:
    a sensor attached to an apparatus, which is configured for insertion within the anatomical structure, wherein the apparatus comprises an elongated guidewire and at least one set of mechanically biased legs distributed along a length of the guidewire, wherein the at least one set of mechanically biased legs extend outwardly from respective first ends thereof that are attached to the guidewire and terminate in respective distal ends of the at least one set of mechanically biased legs, each set of mechanically biased legs being mechanically biased to retain the guidewire at a central location between the distal ends thereof when engaging contact locations along an interior wall of the anatomical structure;
    a tracking system that generates tracking data representing at least a position of the sensor in a three-dimensional tracking coordinate system over time; and a computing device that includes a processor to execute machine-readable instructions, the instructions to at least:
    compute a motion model characterizing a behavior of the anatomical structure over a time interval based on at least one free parameter and a temporal parameter, the free parameter estimating geometry of the anatomical structure derived from the tracking data, and the temporal parameter indexing the free parameter over the time interval; and
    generate a graphical representation of the motion model to visualize the behavior of the anatomical structure over the time interval.

2. The system of claim 1, wherein the anatomical structure is a tubular structure having a lumen, and
    wherein the sensor is positioned along the lumen of the tubular structure.

3. The system of claim 2, wherein the motion model includes a centerline model for the tubular structure, and for each time instance in the time interval, the instructions are further programmed to:
    determine a series of geometric knots along a centerline of the lumen based on the position of each sensor provided by the tracking data; and
    compute a spline corresponding to the free parameter for each of the geometric knots.

4. The system of claim 3, wherein the motion model includes a surface model for the tubular structure, and for each time instance in the time interval, the instructions are further programmed to:
    loft between circular boundaries for each of the geometric knots, the circular boundaries being sized based on a diameter of the tubular structure.

5. The system of claim 4, wherein the instructions are further programmed to compute a spline corresponding to a tangential free parameter that defines a cross-sectional shape of the tubular structure that changes over the time interval according to the temporal parameter.

6. The system of claim 4, wherein the diameter of the tubular structure is determined from at least one of image data of anatomical structure or the tracking data by computing a distance between a pair of diametrically opposed sensors that engage an interior wall of the lumen.

7. The system of claim 1, wherein the sensor comprises a plurality of sensors distributed along the length of the guidewire from a distal end of the guidewire to an intermediate location spaced from the distal end, the tracking data representing a position of each sensor in the three-dimensional tracking coordinate system over time.

8. The system of claim 1, wherein each of the legs includes a respective sensor at its distal end configured to engage the contact locations along the interior wall of the anatomical structure, and
    wherein the instructions are further programmed to determine a diameter of the anatomical structure for a respective sensor station based on the position of each of the sensors associated with the respective sensor station.

9. The system of claim 1, wherein the tracking system is an electromagnetic tracking system, and
    wherein each sensor is coupled to provide sensor signals to the tracking system in response to an interrogation field provided by the tracking system, the tracking system generating the tracking data based on the sensor signals.

10. The system of claim 1, wherein the temporal parameter comprises a cyclical anatomical function, and
    wherein the instructions are further programmed to time correlate the motion model with a phase of the anatomical function, such that the graphical representation of the motion model is gated to the anatomical function.

11. The system of claim 10, wherein the anatomical function is at least one of a cardiac cycle or a respiratory cycle, the phase of the anatomical function being determined based on input data corresponding to the anatomical function.

12. The system of claim 1, wherein the instructions are further programmed to register image data, which represents a graphical image of the anatomical structure, with the tracking coordinate system and to overlay the registered graphical image of the anatomical structure over the graphical image of the anatomical structure to visualize the behavior of the anatomical structure relative to the graphical image thereof.

13. The system of claim 1, wherein the instructions are further programmed to combine the motion model and a static model of the anatomical structure and thereby generate a composite model in which the motion model provides deformation parameters to describe spatial changes for a portion of the anatomical structure during the time interval.

14. The system of claim 13, wherein the static model comprises a parametric model derived from image data prior to the tracking data being generated.

15. The system of claim 1, wherein at least some of the legs including sensors at their distal ends to be moveable with the wall of the anatomical structure.

16. A method comprising:
    storing tracking data in memory, the tracking data being generated by a tracking system to represent at least a location of at least one sensor in a three-dimensional tracking coordinate system over time while fixed relative to an anatomical structure of a patient, the at least one sensor disposed on an apparatus comprising an elongated guidewire and at least one set of mechanically biased legs extending outwardly from the guidewire and distributed along a length of the guidewire, wherein the at least one set of mechanically biased legs extend outwardly from respective first ends thereof that are attached to the guidewire and terminate in distal ends of the at least one set of mechanically biased legs, each set of mechanically biased legs being mechanically biased to retain the guidewire at a central location between the distal ends thereof when engaging contact locations along an interior wall of the anatomical structure;
    generating a motion model characterizing a spatial behavior of the anatomical structure over a plurality of time instances, the motion model including at least one free parameter and a temporal parameter, each free parameter estimating geometry of the anatomical structure derived from the tracking data, and the temporal parameter indexing the free parameter over the plurality of time instances; and
    generating a visualization that provides a sequence of graphical images based on the motion model to characterize behavior of the anatomical structure over time.

17. The method of claim 16, further comprising time correlating the motion model in visualization with a phase of anatomical function of the patient such that the visualization is gated to the anatomical function.

18. The method of claim 17, further comprising receiving input data corresponding to the anatomical function, wherein the anatomical function includes a cardiac cycle or a respiratory cycle.

19. The method of claim 16, wherein the anatomical structure comprises an elongated tubular structure that includes a lumen, the tracking data being generated while the at least one sensor resides within the lumen.

20. The method of claim 19, wherein the motion model includes a centerline model for the tubular structure, and for each of the time instances, the method further comprises:
determining a series of geometric knots along a centerline of the lumen based the on the location of each sensor provided in the tracking data; and
computing a spline corresponding to the free parameter for each of the geometric knots.

21. The method of claim 20, wherein the motion model further comprises a surface model for the tubular structure, and for each of the time instances, the method further comprises lofting between circular boundaries for each of the geometric knots to represent the outer surface of the tubular structure.

22. The method of claim 21, further comprising computing a spline corresponding to a tangential free parameter that defines a cross-sectional shape of the tubular structure that changes over a sequence of the time instances according to the temporal parameter.

23. The method of claim 22, a dimension of each circular boundary is set based on a diameter of the tubular structure, which is determined from at least one of image data of anatomical structure or the tracking data.

24. The method of claim 16, further comprising:
storing image data that represents a graphical image of the anatomical structure;
spatially registering the image data with the motion model; and
overlaying the visualization over the graphical image of the anatomical structure to display the behavior of the anatomical structure relative to the graphical image thereof.

25. The method of claim 16, further comprising:
storing in memory a static model, the static model comprising a parametric model of the anatomical structure;
combining the motion model and the static model of the anatomical structure and thereby generate a composite model in which the motion model provides deformation parameters to describe spatial changes for a portion of the anatomical structure over time.

26. The method of claim 25, wherein the static model is derived from image data acquired for the anatomical structure prior to generating the tracking data.

27. The method of claim 16, wherein the motion model is a first motion model generated for a first time interval, the method further comprising:
generating a second motion model for the anatomical structure during a second time interval;
computing a difference between the first motion model and the second motion model; and
generating a visualization of the computed difference to characterize changes in the behavior of the anatomical structure between the first and second time intervals.

28. The method of claim 16, wherein the sensor comprises a plurality of sensors distributed along a length of the guidewire from a distal end of the guidewire to an intermediate location spaced from the distal end, the guidewire being positioned within the anatomical structure such that the tracking data represents the location of each sensor in the three-dimensional tracking coordinate system over time.

29. The method of claim 16, wherein at least some of the legs including sensors at their distal ends to be moveable with the wall of the anatomical structure.

* * * * *